United States Patent [19]
Fujiwara et al.

[11] Patent Number: 6,015,909
[45] Date of Patent: Jan. 18, 2000

[54] ARYLIDENE COMPOUND AND SILVER HALIDE PHOTOGRAPHIC MATERIAL

[75] Inventors: Toshiki Fujiwara; Seiji Yamashita; Keiichi Suzuki, all of Kanagawa, Japan

[73] Assignee: Fuji Photo Film Co., Ltd., Kanagawa, Japan

[21] Appl. No.: 08/922,519

[22] Filed: Sep. 3, 1997

[30] Foreign Application Priority Data

Sep. 3, 1996 [JP] Japan ..................................... 8-233466
Mar. 31, 1997 [JP] Japan ..................................... 9-098080

[51] Int. Cl.$^7$ .................................................. C07D 261/12
[52] U.S. Cl. .............................................................. 548/243
[58] Field of Search ............................................... 548/243

[56] References Cited

FOREIGN PATENT DOCUMENTS 0412379  2/1991  European Pat. Off. .
5053241  3/1993  Japan .

Primary Examiner—Joseph K. McKane
Attorney, Agent, or Firm—Birch, Stewart, Kolasch & Birch, LLP

[57] ABSTRACT

An arylidene compound is represented by the following formula (I):

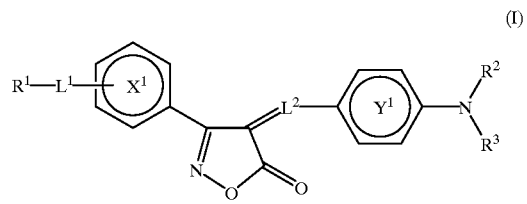

in which $L^1$ is a divalent linking group comprising at least one —NH— and at least one of —CO— and —SO$_2$—; $L^2$ is monomethine, trimethine or pentamethine; $R^1$ is an alkyl group, an aryl group or a heterocyclic group; each of $R^2$ and $R^3$ independently is hydrogen, an alkyl group or an aryl group, and the number of the total carbon atoms contained in $R^2$ and $R^3$ is not more than 20. A silver halide photographic material containing an arylidene dye is also disclosed.

15 Claims, No Drawings

ARYLIDENE COMPOUND AND SILVER
HALIDE PHOTOGRAPHIC MATERIAL

FIELD OF THE INVENTION

The present invention relates to an arylidene compound and a silver halide photographic material containing an arylidene dye.

BACKGROUND OF THE INVENTION

A silver halide photographic material usually contains a dye to color a silver halide emulsion layer or a non-light-sensitive hydrophilic colloidal layer. The dye absorbs light of a specific wavelength.

A non-light-sensitive hydrophilic colloidal layer can contain a dye to control spectrum of light incident on a silver halide emulsion layer provided between the hydrophilic colloidal layer and a support. The hydrophilic colloidal layer functions as a filter layer. A silver halide photographic material can have a filter layer between two silver halide emulsion layers.

Light incident on an emulsion layer is reflected at an interface between the emulsion layer and a support or at the backing surface of the support. The reflected light is incident again on the emulsion layer to cause image blurring, namely halation. An antihalation layer is provided between a support and an emulsion layer or on the backing side of the support to prevent halation. The antihalation layer is a non-light-sensitive hydrophilic colloidal layer containing a dye (a colored layer).

A silver halide emulsion layer may be colored with a dye (antiirradiation dye) to prevent irradiation, which is caused by scattered light. The irradiation reduces the sharpness of the obtained image.

The hydrophilic colloidal layer to be colored usually contains a dye. The dye must satisfy the following conditions:

(1) The dye has a spectral absorption suitable for its use.
(2) The dye is an inactive chemical compound in photographic reactions. For example, the dye should not have adverse chemical effects on silver halide emulsion layers. The adverse effects include reduction of sensitivity, regression of latent image and fog.
(3) The dye is bleached or dissolved in a processing solution or a washing water. The dye should not remain in the processed photographic material.
(4) The dye is not diffused from the colored layer to the other layers.
(5) The dye is stable in a solution or in a photographic material. The color formed by the dye should not be faded nor discolored.

The condition (4) is particularly necessary where the dyes are used in a filter layer or an antihalation layer provided on the side of the emulsion layers. If the dyes are diffused from the colored layers to other layers, the dyes cause adverse spectral effects on the other layers. Further, the diffused dyes degrade the functions of the filter layer or the antihalation layer. However, the dyes tend to be diffused because the colored layer and the other layers are contacted under wet conditions when the layers are formed. Therefore, the photographic materials have been improved to prevent the dyes from diffusing.

For example, each of U.S. Pat. Nos. 2,548,564, 3,625,694 and 4,124,386 discloses a mordant, which has a function of localizing a dye in a specific layer by an interaction between the dye molecule and the mordant. The mordant is a hydrophilic polymer having an electric charge reverse to the charge of an ionized anionic dye. However, it is difficult to remove or bleach the dye, namely to satisfy the condition (3) in the case of using the mordant.

Further, Japanese Patent Provisional Publication Nos. 55(1980)-155350, 55(1980)-155351, 56(1981)-12639, 63(1988)-27838, 63(1988)-197943, European Patent Nos. 15601, 274723, 276566, 299435, U.S. Pat. No. 4,950,586 and International Patent Publication No. WO88/04794 disclose a layer colored with solid particles of a water-insoluble dye. However, a dye should be stirred for a long term to prepare solid particle dispersion of the dye. Even though a dye is used in the form of solid particles, the particles are sometimes diffused from the colored layer to other layers.

Japanese Patent Provisional Publication No. 5(1993)-53242 discloses a silver halide photographic material, which contains an oily composition (oily droplets of an organic solvent) or a polymer latex composition (polymer particles) of 4-(pyrrole-3-yl-methylidene)-pyrazoline-5-one or 4-(indole-3-yl-methylidene)-pyrazoline-5-one (dye). The oily droplets or polymer particles containing a dye are not diffused from a colored layer to other layers. Accordingly, the dyes disclosed in the publication satisfy the condition (4).

It is generally difficult to remove or bleach a dye contained in the oily droplets or the polymer particles at a photographic process. Japanese Patent Provisional Publication No. 5(1993)-53242 discloses exceptional dyes, which can be removed from the oily droplets or polymer particles. Accordingly the dyes disclosed in the publication further satisfy the condition (3). However, the dyes disclosed in the publication cannot be used as magenta or cyan dyes because the dyes have a short absorption maximum wavelength. Even if the dyes are used as yellow dyes, the dyes have a problem that a color remains in the formed image after a rapid process or a process of using a solution of a low concentration of sulfite ion.

Japanese Patent Provisional Publication No. 3(1991)-72340 discloses dyes, which can be contained in an oily composition or a polymer latex composition. However, it is difficult to remove or bleach the dyes contained in oily droplets or polymer particles at a photographic process. Accordingly, the publication proposes an exceptional use of a dye, which does not satisfy the condition (3). The dye remains in the formed image. For example, the dye is used for color correction of the formed image.

SUMMARY OF THE INVENTION

If a dye can be added to oily droplets of an organic solvent or polymer particles in the same manner as is described in Japanese Patent Provisional Publication No. 5(1993)-53242, the dye is not diffused from a colored layer to other layers to satisfy the condition (4). If a dye can be removed or bleached from the oily droplets or the polymer particles after image formation, the dye does not remain in the formed image to satisfy the condition (3). Such convenient dyes have been disclosed only in Japanese Patent Provisional Publication No. 5(1993)-53241. Further, the dyes disclosed in the publication have the above-mentioned problems.

The applicants have searched for convenient dyes, which can be added to oily droplets or particles, and can also be removed or bleached from the oily droplets or particles. Many dyes have been proposed in the photographic technical field. Further, various dyes have been proposed in other technical fields. For example, Japanese Patent Provisional Publication No. 54(1979)-24024 and U.S. Pat. No. 4,166,740 disclose dyes to be used in electrophoresis. However, the applicants do not find out such convenient dyes as is disclosed in Japanese Patent Provisional Publication No. 5(1993)-53241. Now, the applicants synthesize new dyes in place of searching the known dyes.

An object of the present invention is to provide a silver halide photographic material having a layer selectively colored with a dye, which can quickly be removed or bleached at a development process.

Another object of the invention is to provide a dye, which can be added to oily droplets or polymer particles, and can also be removed or bleached from the droplets or particles.

A further object of the invention is to provide an arylidene compound, which can advantageously be used as a dye in a silver halide photographic material.

The present invention provides an arylidene compound represented by the formula (I):

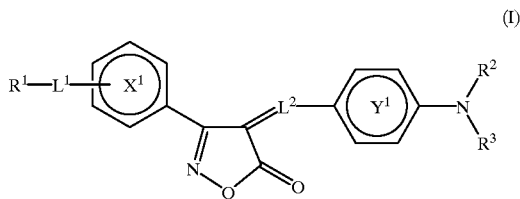

in which $L^1$ is a divalent linking group comprising at least one —NH— and at least one of —CO— and —SO$_2$—; $L^2$ is monomethine, trimethine or pentamethine, each of which may be substituted with an alkyl group, an alkoxy group, amino, an alkylamino group, an amido group or an aryl group; $R^1$ is an alkyl group, an aryl group or a heterocyclic group, each of which may be substituted with a halogen atom, cyano, hydroxyl, an alkyl group, an alkoxycarbonyl group, an aryl group, a heterocyclic group, amino, an alkylamino group, an acyl group, an amido group, a sulfonamido group, a carbamoyl group or a sulfamoyl group; each of $R^2$ and $R^3$ independently is hydrogen, an alkyl group or an aryl group, the number of the total carbon atoms contained in $R^2$ and $R^3$ is not more than 20, and the alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group; the benzene ring $X^1$ may be further substituted with a halogen atom, cyano, hydroxyl, an alkyl group substituted with a halogen atom, an alkoxy group, an alkoxycarbonyl group, an acyl group, a sulfonamido group or a sulfamoyl group; and the benzene ring $Y^1$ may be further substituted with an alkyl group, an alkoxy group, an aryl group, amino, an alkylamino group or an amido group.

The invention also provides an arylidene compound represented by the formula (II):

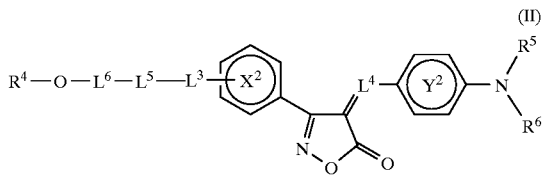

in which $L^3$ is a divalent linking group comprising at least one —NH— and at least one of —CO— and —SO$_2$—; $L^4$ is monomethine, trimethine or pentamethine, each of which may be substituted with an alkyl group, an alkoxy group, amino, an alkylamino group, an amido group or an aryl group; $L^5$ is an alkylene group or an arylene group, each of which may be substituted with a halogen atom or hydroxyl; $L^6$ is a divalent linking group selected from the group consisting of —NH—, —O—, —CO—, —SO$_2$—, an alkylene group, an arylene group and a combination thereof, and the alkylene group and the arylene group may be substituted with a halogen atom or hydroxyl; $R^4$ is hydrogen or an alkyl group; each of $R^5$ and $R^6$ independently is hydrogen, an alkyl group or an aryl group, the number of the total carbon atoms contained in $R^5$ and $R^6$. is not more than 20, and the alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group; the benzene ring $X^2$ may be further substituted with a halogen atom, cyano, hydroxyl, an alkyl group substituted with a halogen atom, an alkoxy group, an alkoxycarbonyl group, an acyl group, a sulfonamido group or a sulfamoyl group; and the benzene ring $Y^2$ may be further substituted with an alkyl group, an alkoxy group, an aryl group, amino, an alkylamino group or an amido group.

The invention further provides a silver halide photographic material comprising a support, a silver halide emulsion layer and a non-light-sensitive hydrophilic colloidal layer, wherein the silver halide emulsion layer or the hydrophilic colloidal layer contains an arylidene dye represented by the above-mentioned formula.

In the silver halide photographic material, oily droplets of an organic solvent or particles of a polymer are preferably dispersed in the silver halide emulsion layer or the hydrophilic colloidal layer. The arylidene dye represented by the formula (I) is preferably contained in the oily droplets or particles.

The arylidene compound can advantageously be used as a dye in a silver halide photographic material to color a layer selectively. Further, the arylidene dye can quickly be removed or bleached at a development process. The effect of the invention is particularly remarkable in the case that the arylidene dye is contained in the oily droplets or particles.

DETAILED DESCRIPTION OF THE INVENTION

The arylidene compound of the present invention is represented by the formula (I).

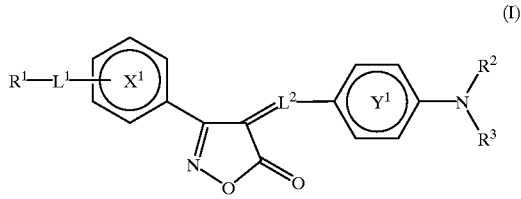

In the formula (I), $L^1$ is a divalent (amido bond type) linking group comprising at least one —NH— and at least one of —CO— and —SO$_2$—. Examples of the combinations include —NHCO—, —CONH—, —NHSO$_2$—, —SO$_2$NH—, —SO$_2$NHCO— and —CONHSO$_2$—(wherein the left side is attached to $R^1$, and the right side is attached to the benzene ring $X^1$).

$L^1$ is attached to the benzene ring $X^1$ preferably at the meta or para position rather than the ortho position to the position at which the 5-isoxazolone ring is attached to the benzene ring $X^1$. The para position is most preferred.

In the formula (I), $L^2$ is monomethine, trimethine or pentamethine. Each of the methines may be substituted with an alkyl group (e.g., methyl, ethyl), an alkoxy group (e.g., methoxy, ethoxy), amino, an alkylamino group (e.g., methylamino, dimethylamino), an amido group (e.g., acetamido) or an aryl group (e.g., phenyl, m-methylsulfonamidophenyl). In the case that the trimethine or the pentamethine is substituted, the substituent group is preferably attached to the nearest methine of the 5-isoxazolone ring. $L^2$ preferably is monomethine, trimethine or pentamethine, each of which has no substituent groups.

In the formula (I), $R^1$ is an alkyl group, an aryl group or a heterocyclic group, preferably is an alkyl group or an aryl group, and more preferably is an aryl group.

The alkyl group preferably has 1 to 18 carbon atoms. The alkyl group preferably has a chain structure rather than a cyclic structure. The alkyl group of the chain structure may be branched. Examples of the alkyl groups include methyl, ethyl and propyl.

The aryl group preferably has 6 to 22 carbon atoms. Examples of the aryl groups include phenyl and naphthyl.

The hetrocyclic group preferably has five or six-membered saturated or unsaturated heterocyclic ring. An aliphatic ring, an aromatic ring or another heterocyclic ring may be condensed with the five or six-membered hetrocyclic ring. Examples of the heterocyclic rings (including condensed rings) include pyrrole ring, imidazole ring, triazole ring, thiadiazole ring, tetrazole ring, thiazole ring, isothiazole ring, pyrazole ring, oxazole ring, isooxazole ring, selenazole ring, pyridine ring, pyrimidine ring, pyridazine ring, triazine ring, guinoxaline ring, tetrazaindene ring, oxadiazole ring, selenadiazole ring, indazole ring, triazaindene ring, tellurazole ring, indole is ring, isoindole ring, indolenine ring, chromene ring, chroman ring, quinoline ring, isoquinoline ring, quinolizine ring, cinnoline ring, phthalazine ring, quinazoline ring, naphthyridine ring, purine ring, pteridine ring, indolizine ring, furan ring, thiophene ring, pyran ring, azepine ring and oxazine ring.

The alkyl group, the aryl group and the heterocyclic group may be substituted with a halogen atom, cyano, hydroxyl, an alkyl group, an alkoxycarbonyl group, an aryl group, a heterocyclic group, amino, an alkylamino group, an acyl group, an amido group, a sulfonamido group, a carbamoyl group or a sulfamoyl group.

Examples of the substituted alkyl groups include ethoxycarbonylmethyl, 2-cyanoethyl, 2-propionamidoethyl, dimethylaminomethyl, di(methoxycarbonylmethyl) aminopropyl, benzyl and phenacyl.

Examples of the substituted aryl groups include 2-methoxy-5-ethoxycarbonylphenyl, 4-di(ethoxycarbonylmethyl)carbamoylphenyl, 3-ethoxyethoxyethoxycarbonylphenyl, 3-methoxyethoxycarbonylphenyl, 4-acetylsulfamoylphenyl, 4-propionylsulfamoylphenyl and 4-methanesulfonamidophenyl.

$R^1$ further preferably is a substituted alkyl group or a substituted aryl group, and furthermore preferably is an aryl group substituted with a halogen atom, cyano, hydroxyl, an alkyl group, an alkoxycarbonyl group, a heterocyclic group, amino, an alkylamino group, an acyl group, an amido group, a sulfonamido group, a carbamoyl group or a sulfamoyl group. $R^1$ particularly preferably is an alkyl group or an aryl group substituted with a group having hydroxyl or an alkoxy group at its terminal end. The particularly preferred $R^1$ is described in more detail as $R^4$—O—$L^6$—$L^5$— in the formula (II).

In the formula (I), each of $R^2$ and $R^3$ independently is hydrogen, an alkyl group or an aryl group, preferably is an alkyl group or an aryl group, and more preferably is an alkyl group. The number of the total carbon atoms contained in $R^2$ and $R^3$ (including the carbon atoms contained in substituent groups) is not more than 20, preferably not more than 16, more preferably not more than 12, further preferably not more than 10, and most preferably not more than 8.

The alkyl group preferably has 1 to 12 carbon atoms, more preferably has 1 to 6 carbon atoms, further preferably has 1 to 4 carbon atoms and most preferably has 1 or 2 carbon atoms (namely methyl or ethyl). The alkyl group preferably has a chain structure rather than a cyclic structure. The alkyl group of the chain structure may be branched. Examples of the alkyl groups include methyl, ethyl, cyclohexyl and dodecyl.

The aryl group preferably has 6 to 12 carbon atoms. Examples of the aryl groups include phenyl and naphthyl.

The alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group.

Examples of the substituted alkyl groups include ethoxycarbonylmethyl, hydroxyethyl, hydroxyethoxyethyl, methanesulfonamidoethyl, cyanoethyl, 2,2,3,3-tetrafluoropropyl, chloroethyl, acetoxyethyl and dimethylaminomethyl.

Examples of the substituted aryl groups include 4-methylphenyl, 4-carboxyphenyl and 4-acetylsulfamoylphenyl.

Each of $R^2$ and $R^3$ most preferably is methyl or ethyl, which has no substituent groups.

In the formula (I), the benzene ring $X^1$ may be further substituted with a halogen atom (e.g., chlorine atom, bromine atom, fluorine atom), cyano, hydroxyl, an alkyl group substituted with a halogen atom (e.g., trifluoromethyl), an alkoxy group (e.g., methoxy), an alkoxycarbonyl group, an acyl group, a sulfonamido group or a sulfamoyl group. The substituent group of the benzene ring $X^1$ preferably is an electron attractive group. In more detail, the substituent group preferably has a positive value of Hammett's substituent constant. The most preferred substituent group is chlorine atom.

In the formula (I), the benzene ring $Y^1$ may be further substituted with an alkyl group, an alkoxy group, an aryl group, amino, an alkylamino group or an amido group.

The alkyl group preferably has 1 to 12 carbon atoms. The alkyl group preferably has a chain structure rather than a cyclic structure. The alkyl group of the chain structure may be branched. Examples of the alkyl groups include methyl, ethyl, cyclohexyl and dodecyl.

The alkoxy group preferably has 1 to 12 carbon atoms. The alkyl moiety of the alkoxy group is the same as the above-defined alkyl group. Examples of the alkoxy groups include methoxy, ethoxy, methoxyethoxy and 2-hydroxyethoxy.

The aryl group preferably has 6 to 12 carbon atoms. Examples of the aryl groups include phenyl and naphthyl.

The alkylamino group preferably has 1 to 12 carbon atoms. The alkyl moiety of the alkylamino group is the same as the above-defined alkyl group. Examples of the alkylamino groups include methylamino and dimethylamino.

The amido groups preferably has 2 to 12 carbon atoms. Examples of the amido groups include acetamido.

As is defined above, the substituent groups of the arylidene compound of the formula (I) do not include sulfo, a salt thereof and a salt of carboxyl. The substituent groups are defined above to add the arylidene compound to oily droplets of an organic solvent or polymer particles easily.

In the case that the arylidene compound is used as a dye, the molecular structure of the compound is preferably arranged to increase the solubility in an organic solvent. A photographic material usually uses an organic solvent having a boiling point of 30 to 150° C. The photographic material also uses an organic solvent miscible with water. Examples of the organic solvents having a boiling point of 30 to 150° C. include lower alkyl esters of lower fatty acids (e.g., ethyl acetate, butyl acetate, ethyl propionate, β-ethoxyethyl acetate, methylcellosolve acetate), alcohols (e.g., secondary butanol) and ketones (e.g., methyl isobutyl ketone). Examples of the organic solvents miscible with water include lower alcohols (e.g., methanol, ethanol).

The arylidene compound is preferably represented by the formula (II).

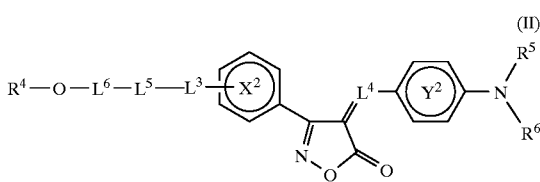

In the formula (II), $L^3$ is a divalent (amido bond type) linking group comprising at least one —NH— and at least one of —CO— and —SO$_2$—. Examples of the combinations include —NHCO—, —CONH—, —NHSO$_2$—, —SO$_2$NH—, —SO$_2$NHCO— and —CONHSO$_2$— (wherein the left side is attached to $L^5$, and the right side is attached to the benzene ring $X^2$).

$L^3$ is attached to the benzene ring $X^2$ preferably at the meta or para position rather than the ortho position to the position at which the 5-isoxazolone ring is attached to the benzene ring $X^2$. The para position is most preferred.

In the formula (II), $L^4$ is monomethine, trimethine or pentamethine. Each of the methines may be substituted with an alkyl group (e.g., methyl, ethyl), an alkoxy group (e.g., methoxy, ethoxy), amino, an alkylamino group (e.g., methylamino, dimethylamino), an amido group (e.g., acetamido) or an aryl group (e.g., phenyl, m-methylsulfonamidophenyl). In the case that the trimethine or the pentamethine is substituted, the substituent group is preferably attached to the nearest methine of the 5-isoxazolone ring. $L^4$ preferably is monomethine, trimethine or pentamethine, each of which has no substituent groups.

In the formula (II), $L^5$ is an alkylene group or an arylene group. The arylene group is particularly preferred.

The alkylene group preferably has 1 to 18 carbon atoms. The alkylene group preferably has a chain structure rather than a cyclic structure. The alkylene group of the chain structure may be branched. Examples of the alkylene groups include methylene, ethylene and propylene.

The arylene group preferably has 6 to 22 carbon atoms. Examples of the arylene groups include phenylene and naphthylene.

The alkylene group and the arylene group may be substituted with a halogen atom or hydroxyl.

In the formula (II), $L^6$ is a divalent linking group selected from the group consisting of —NH—, —O—, —CO—, —SO$_2$—, an alkylene group, an arylene group and a combination thereof. The alkylene group and the arylene group may be substituted with a halogen atom or hydroxyl.

Examples of the combinations (wherein the left side is attached to the oxygen atom and the right side is attached to $L^5$) are shown below.

$L^{61}$: —(an alkylene group)—O—(an alkylene group)—O—CO—

$L^{62}$: —(an alkylene group)—O—CO—

$L^{63}$: —(an alkylene group)—NH—CO— in which the alkylene group may be substituted with a halogen atom or hydroxyl.

$L^6$ preferably is selected from the group consisting of $L^{61}$, $L^{62}$ and $L^{63}$.

In the formula (II), $R^4$ is hydrogen or an alkyl group. Hydrogen is particularly preferred.

The alkyl group preferably has 1 to 4 carbon atoms (methyl, ethyl, propyl, butyl), more preferably has 1 to 3 carbon atoms, further preferably has 1 or 2 carbon atoms, and most preferably has 1 carbon atom (methyl).

In the formula (II), each of $R^5$ and $R^6$ independently is hydrogen, an alkyl group or an aryl group, preferably is an alkyl group or an aryl group, and more preferably is an alkyl group. The number of the total carbon atoms contained in $R^5$ and $R^6$ (including the carbon atoms contained in substituent groups) is not more than 20, preferably not more than 16, more preferably not more than 12, further preferably not more than 10, and most preferably not more than 8.

The alkyl group preferably has 1 to 12 carbon atoms, more preferably has 1 to 6 carbon atoms, further preferably has 1 to 4 carbon atoms and most preferably has 1 or 2 carbon atoms (namely methyl or ethyl). The alkyl group preferably has a chain structure rather than a cyclic structure. The alkyl group of the chain structure may be branched. Examples of the alkyl groups include methyl, ethyl, cyclohexyl and dodecyl.

The aryl group preferably has 6 to 12 carbon atoms. Examples of the aryl groups include phenyl and naphthyl.

The alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group.

Examples of the substituted alkyl groups include ethoxycarbonylmethyl, hydroxyethyl, hydroxyethoxyethyl, methanesulfonamidoethyl, cyanoethyl, 2,2,3,3-tetrafluoropropyl, chloroethyl, acetoxyethyl and dimethylaminomethyl.

Examples of the substituted aryl groups include 4-methylphenyl, 4-carboxyphenyl and 4-acetylsulfamoylphenyl.

Each of $R^5$ and $R^6$ most preferably is methyl or ethyl, which has no substituent groups.

In the formula (II), the benzene ring $X^2$ may be further substituted with a halogen atom (e.g., chlorine atom, bromine atom, fluorine atom), cyano, hydroxyl, an alkyl group substituted with a halogen atom (e.g., trifluoromethyl), an alkoxy group (e.g., methoxy), an alkoxycarbonyl group, an acyl group, a sulfonamido group or a sulfamoyl group. The substituent group of the benzene ring $X^2$ preferably is an electron attractive group. In more detail, the substituent group preferably has a positive value of Hammett's substituent constant. The most preferred substituent group is chlorine atom.

In the formula (II), the benzene ring $Y^2$ may be further substituted with an alkyl group, an alkoxy group, an aryl group, amino, an alkylamino group or an amido group.

The alkyl group preferably has 1 to 12 carbon atoms. The alkyl group preferably has a chain structure rather than a cyclic structure. The alkyl group of the chain structure may be branched. Examples of the alkyl groups include methyl, ethyl, cyclohexyl and dodecyl.

The alkoxy group preferably has 1 to 12 carbon atoms. The alkyl moiety of the alkoxy group is the same as the above-defined alkyl group. Examples of the alkoxy groups include methoxy, ethoxy, methoxyethoxy and 2-hydroxyethoxy.

The aryl group preferably has 6 to 12 carbon atoms. Examples of the aryl groups include phenyl and naphthyl.

The alkylamino group preferably has 1 to 12 carbon atoms. The alkyl moiety of the alkylamino group is the same as the above-defined alkyl group. Examples of the alkylamino groups include methylamino and dimethylamino.

The amido groups preferably has 2 to 12 carbon atoms. Examples of the amido groups include acetamido.

Examples of the arylidene compounds represented by the formula (I) are shown below.

A-1
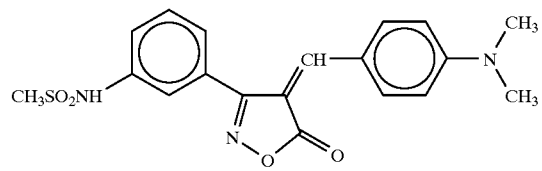

A-2
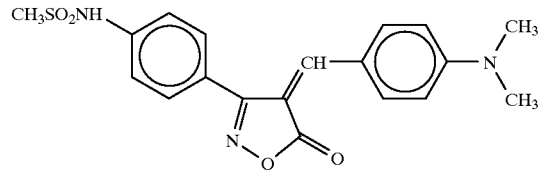

A-3
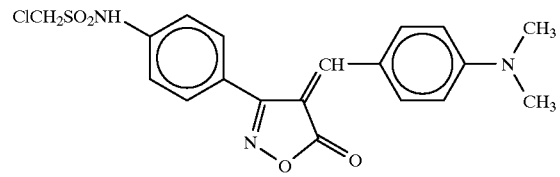

A-4
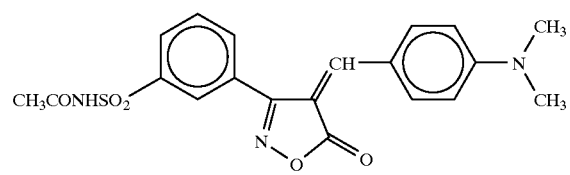

A-5
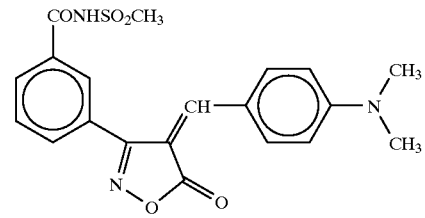

-continued
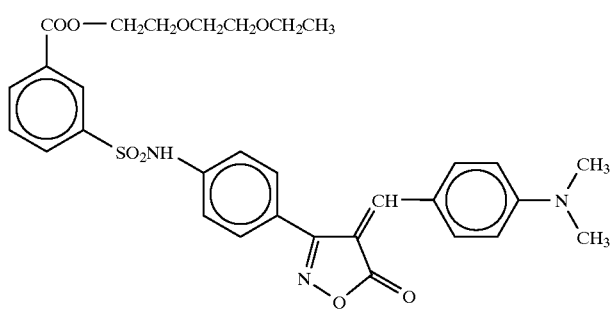
A-6
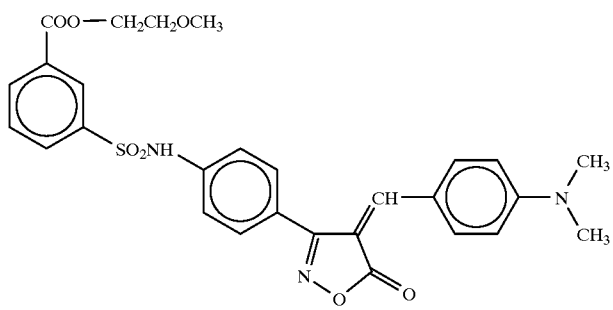
A-7
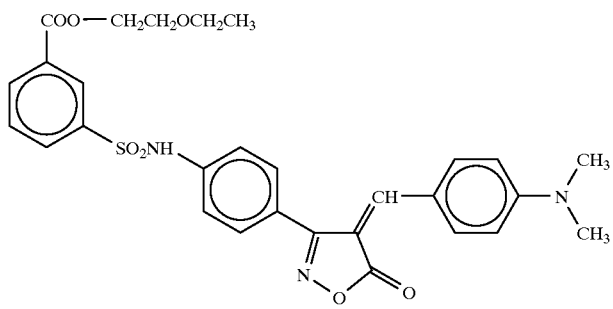
A-8
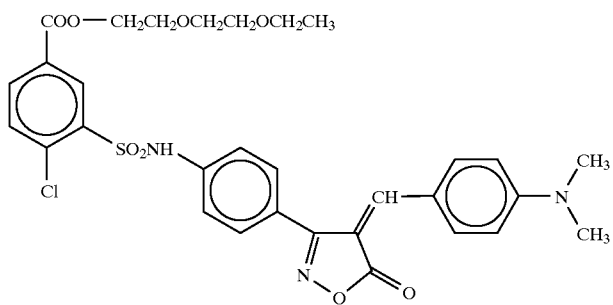
A-9

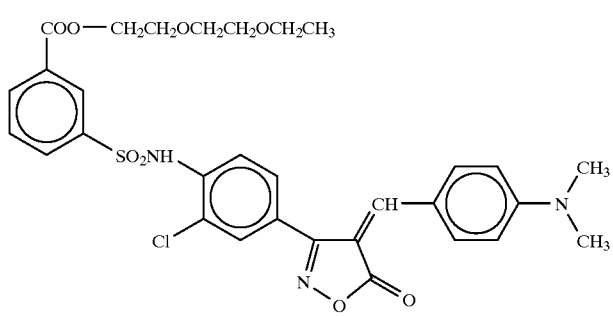
A-10
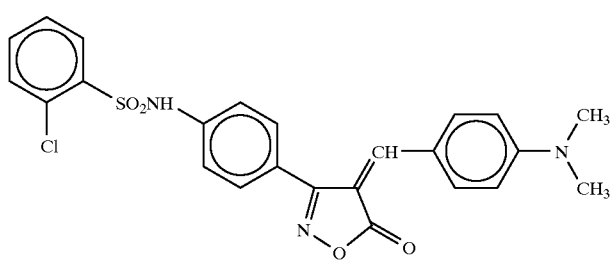
A-11
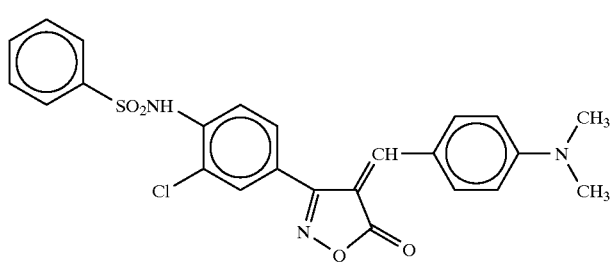
A-12
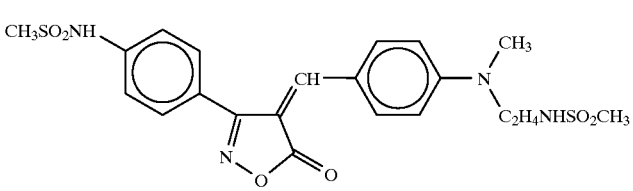
A-13
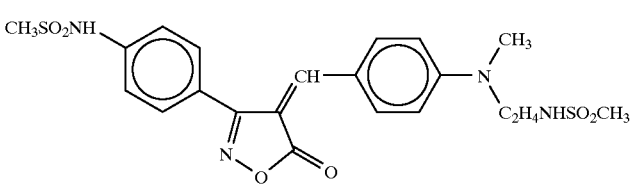
A-14
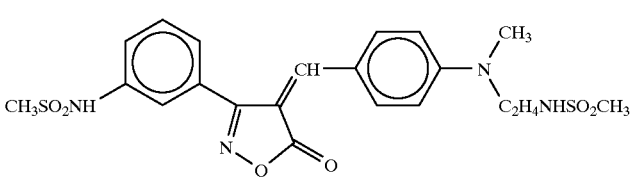
A-15

-continued
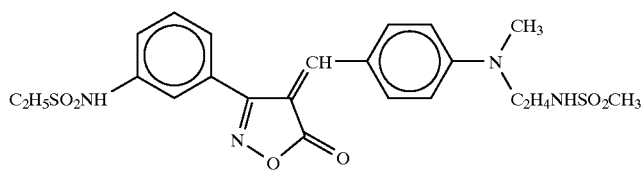
A-16
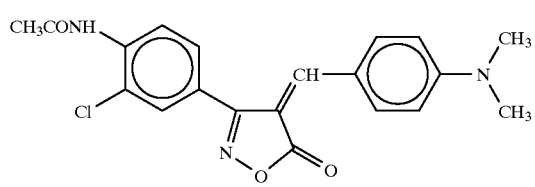
A-17
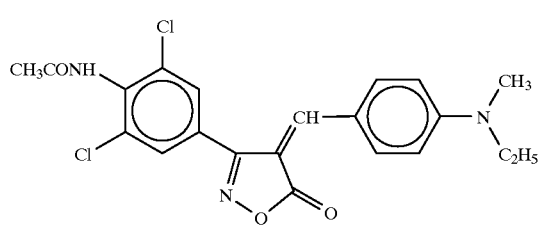
A-18
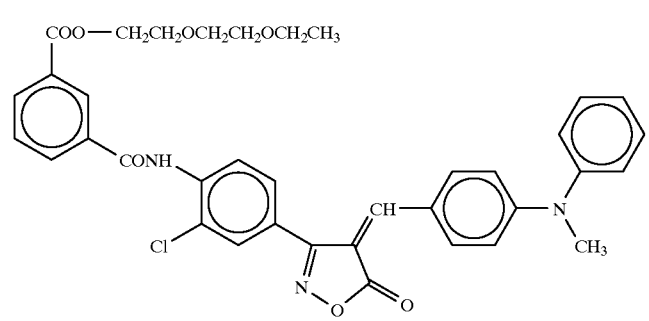
A-19
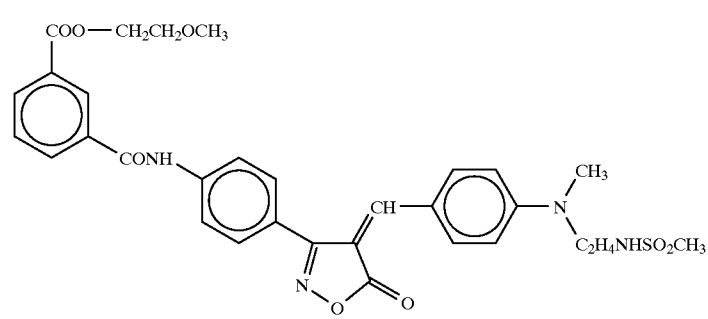
A-20

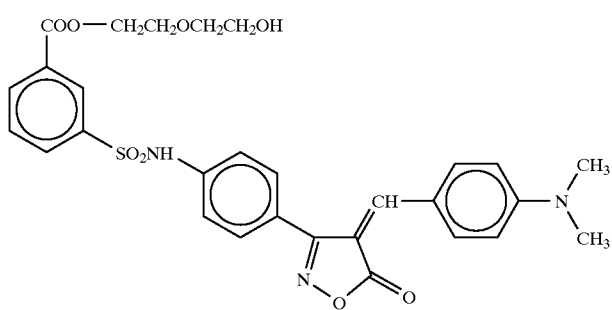
A-21
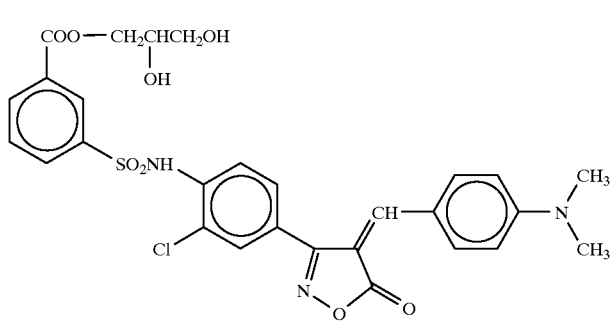
A-22
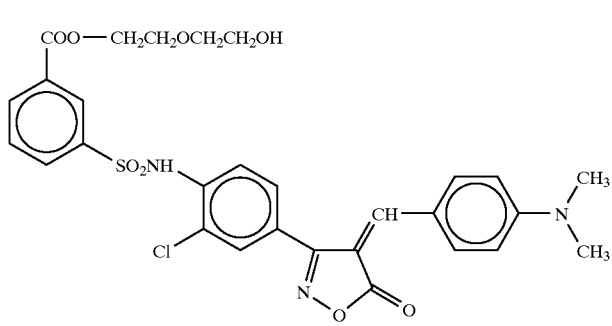
A-23
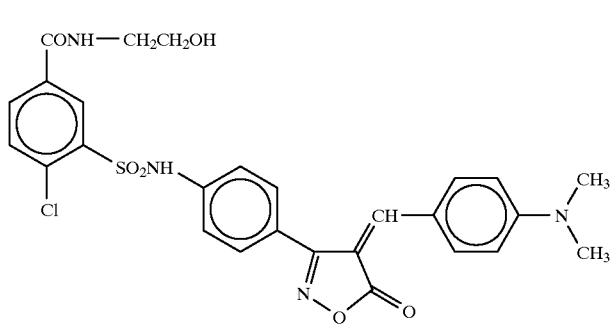
A-24

-continued
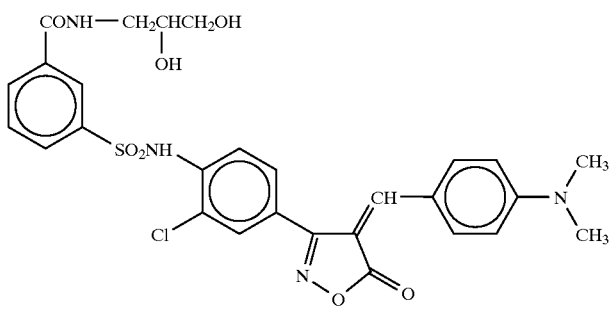
A-25
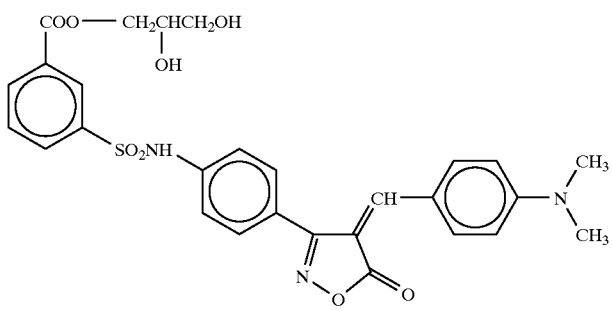
A-26
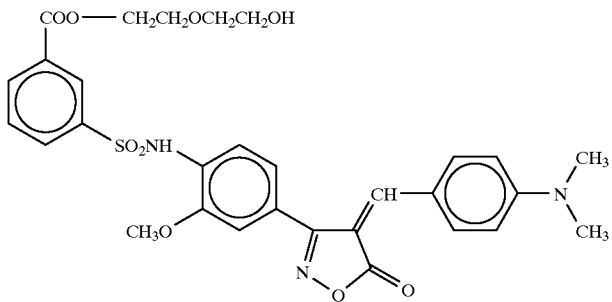
A-27
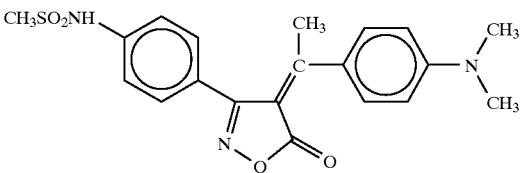
A-28
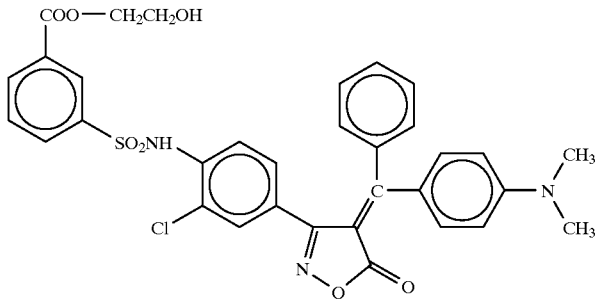
A-29

-continued
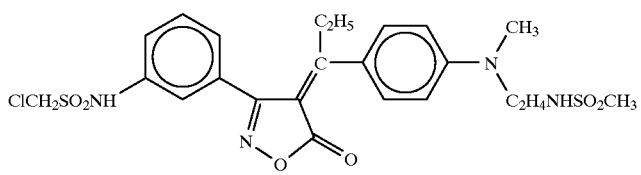
A-30
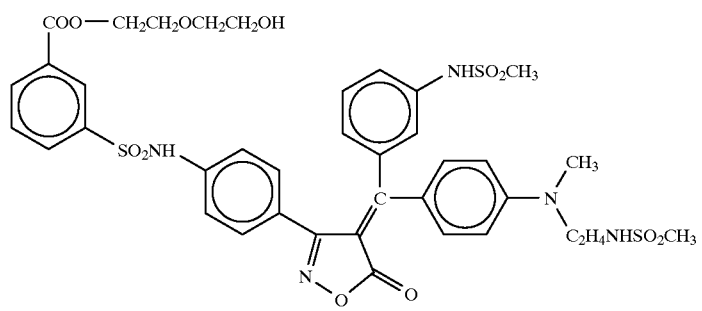
A-31
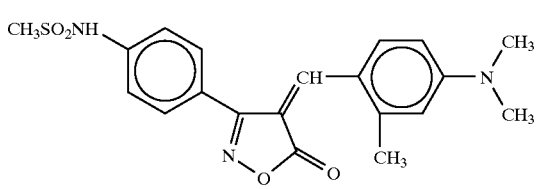
A-32
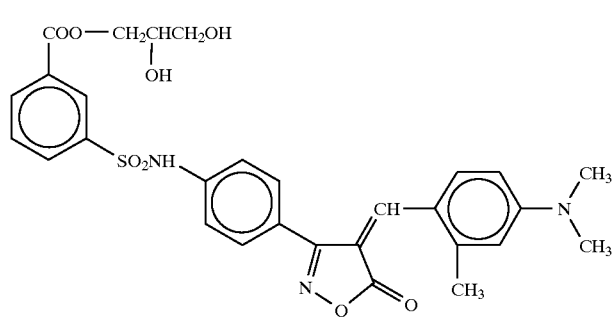
A-33
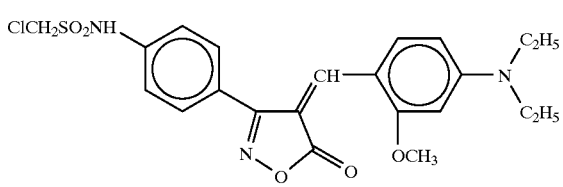
A-34
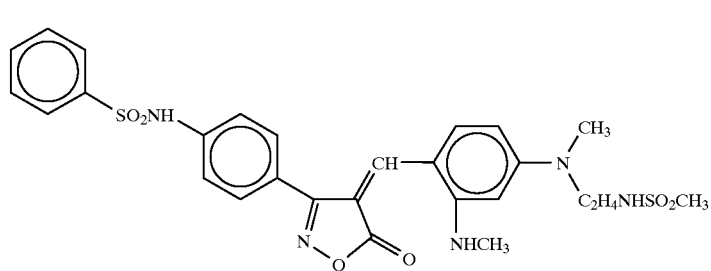
A-35

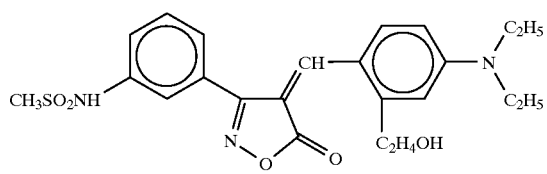
A-36
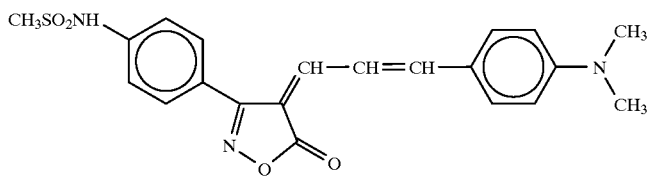
B-1
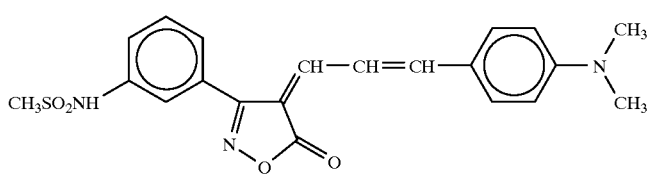
B-2
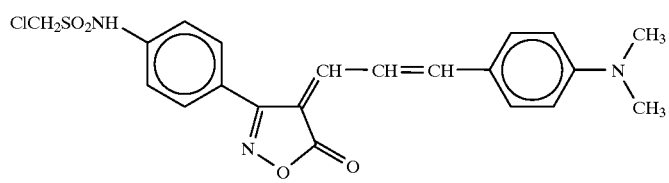
B-3
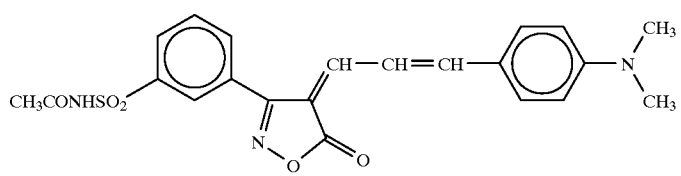
B-4
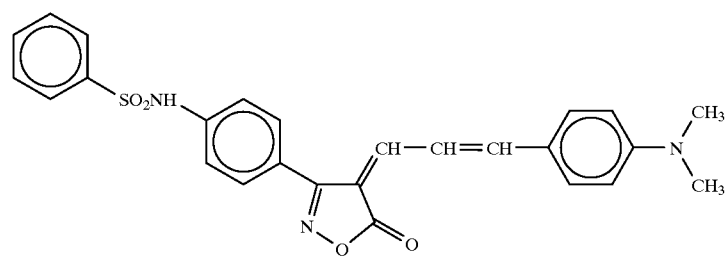
B-5

-continued
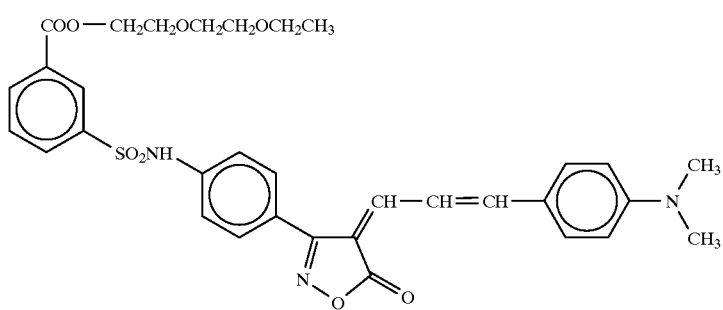
B-6
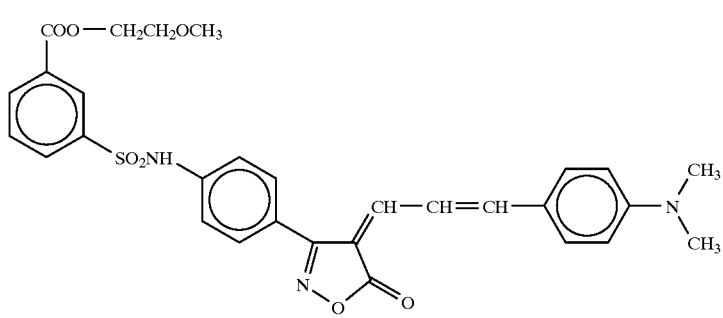
B-7
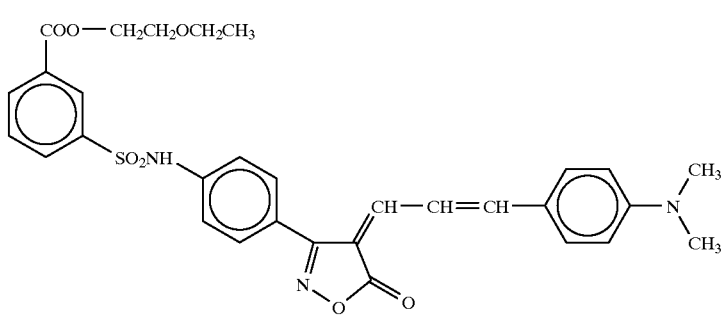
B-8
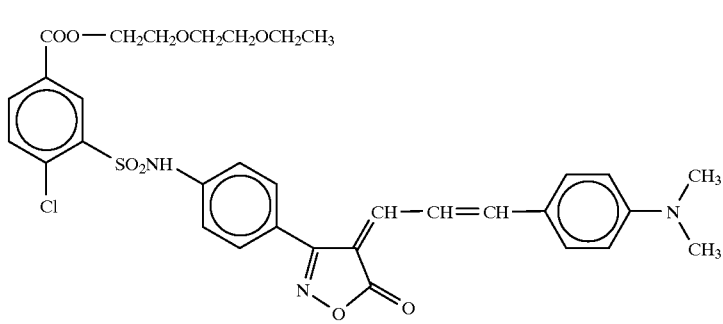
B-9

-continued

B-10, B-11, B-12, B-13, B-14, B-15

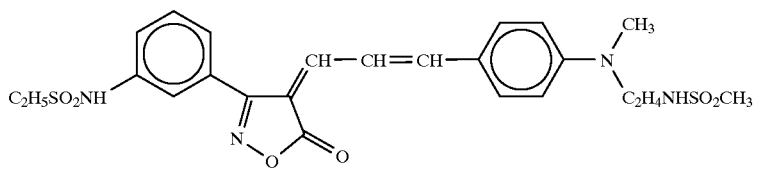
B-16
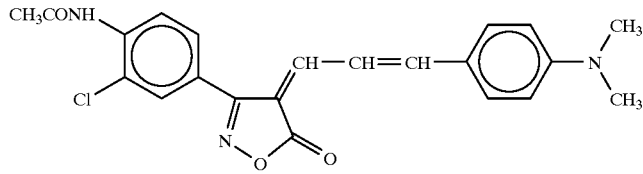
B-17
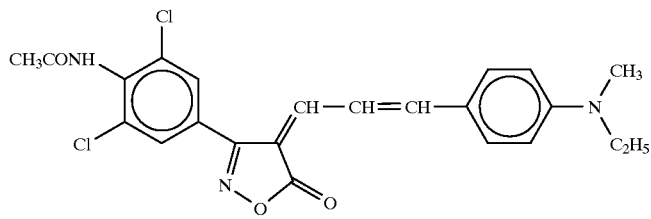
B-18
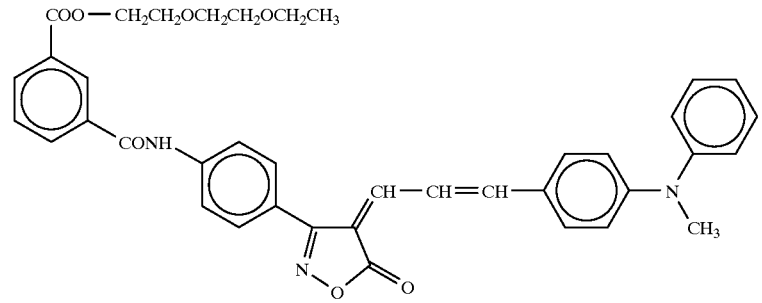
B-19
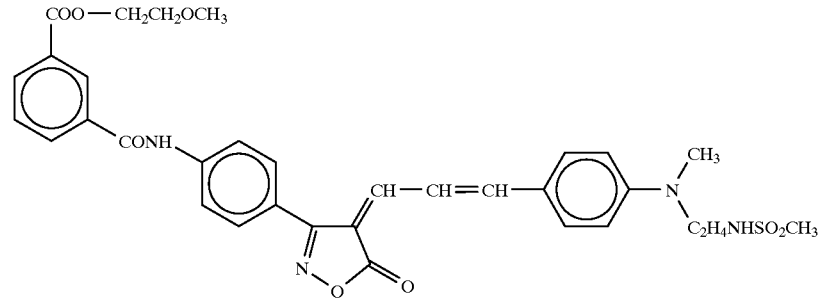
B-20

-continued
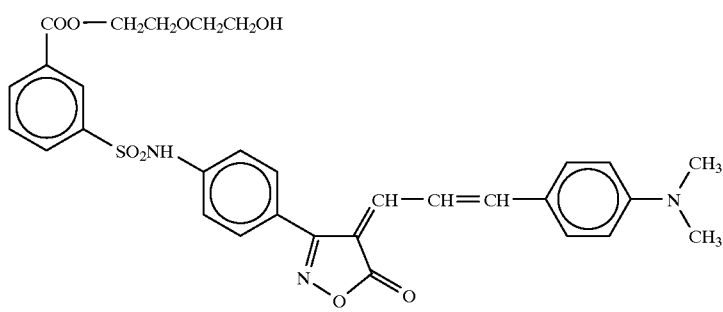
B-21
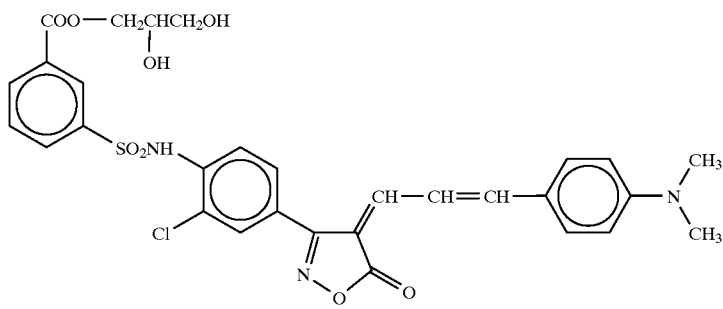
B-22
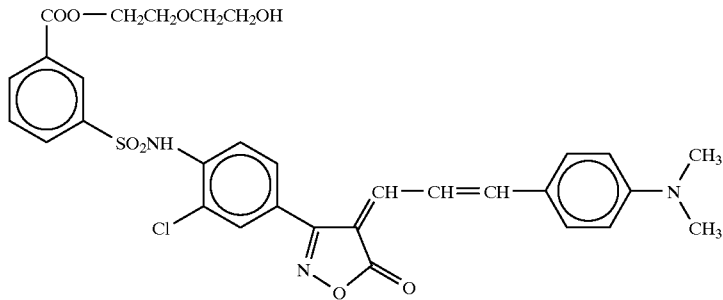
B-23
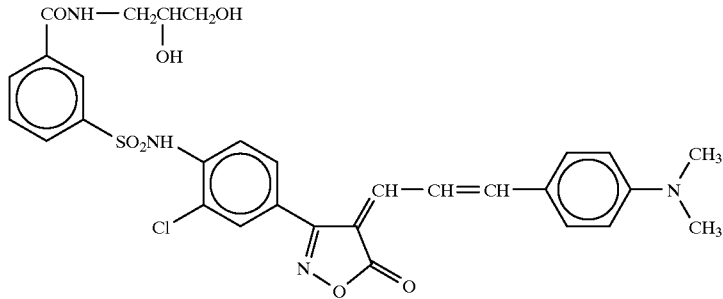
B-24
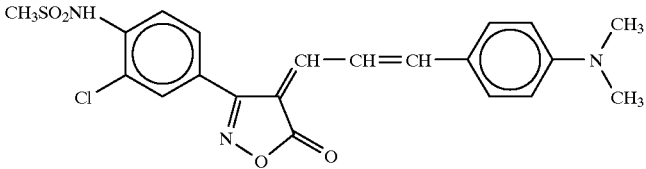
B-25

-continued
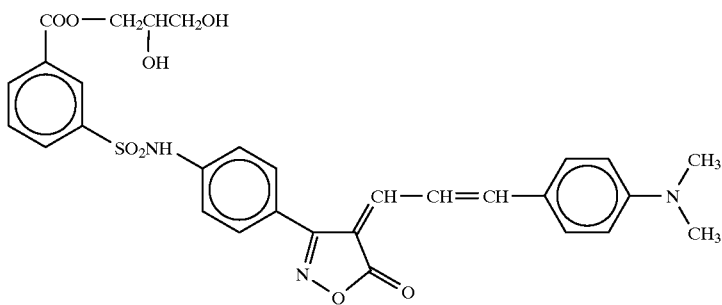
B-26
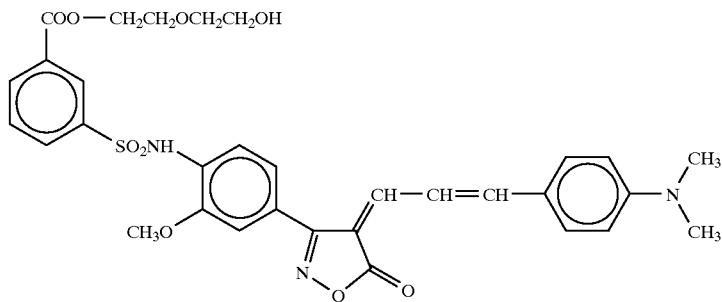
B-27
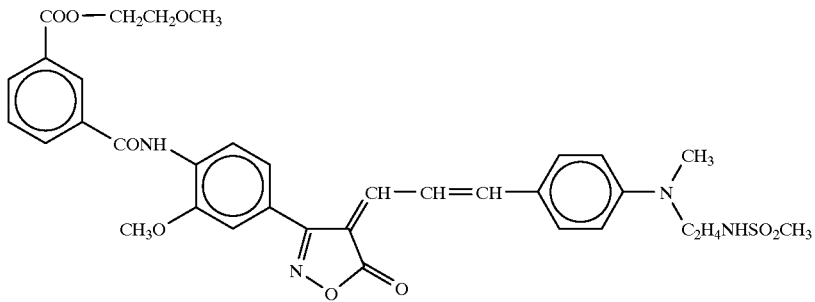
B-28
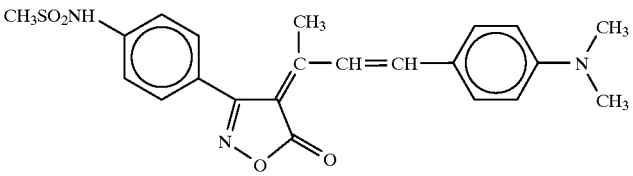
B-29
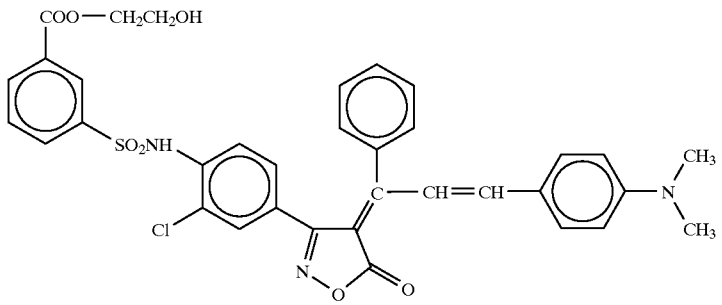
B-30

-continued
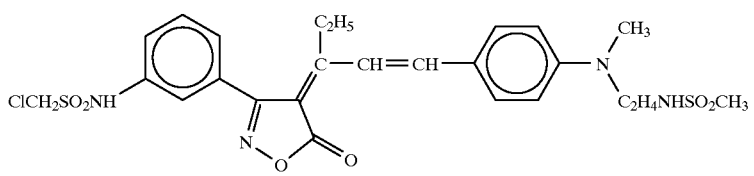
B-31
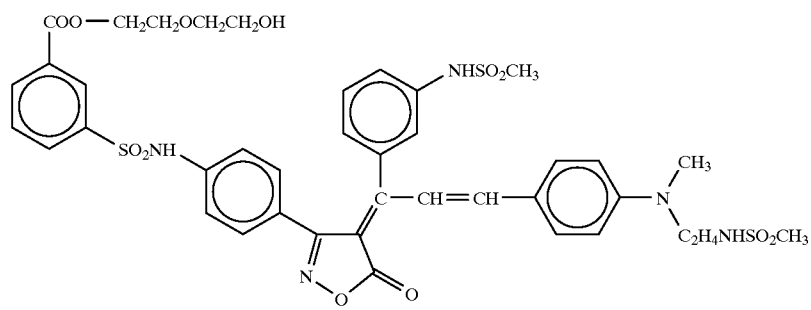
B-32
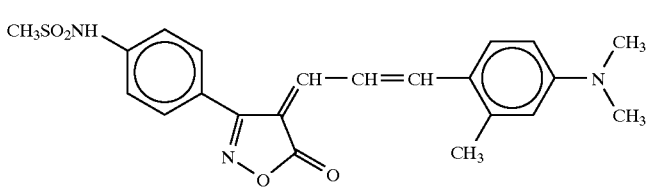
B-33
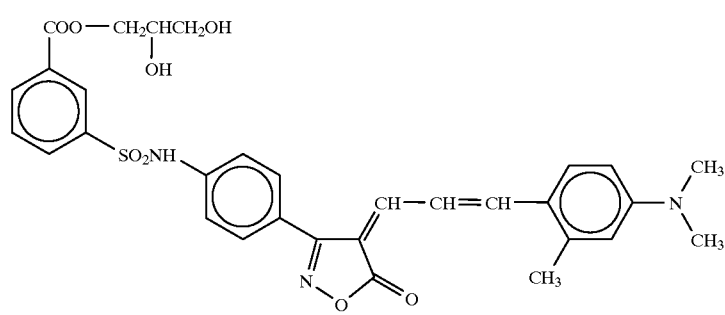
B-34
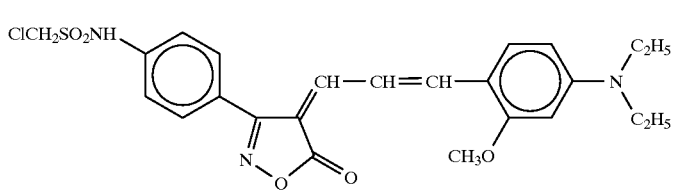
B-35
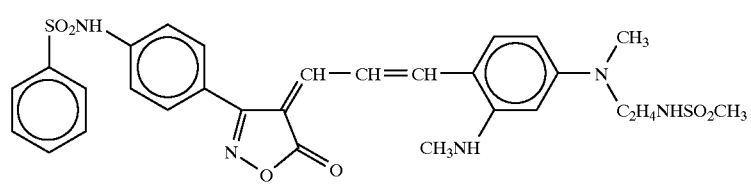
B-36

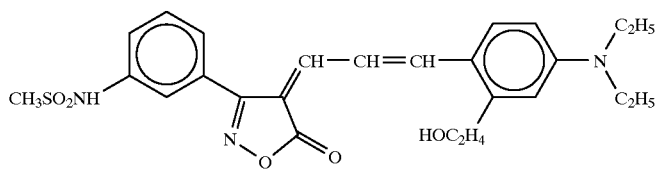
B-37
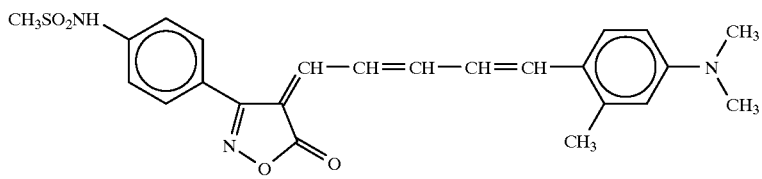
C-1
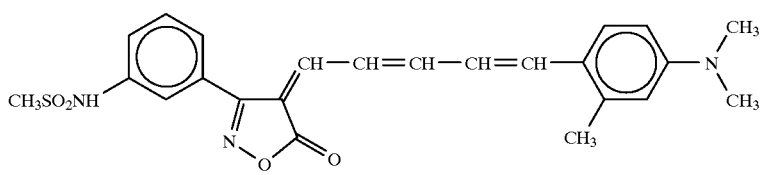
C-2
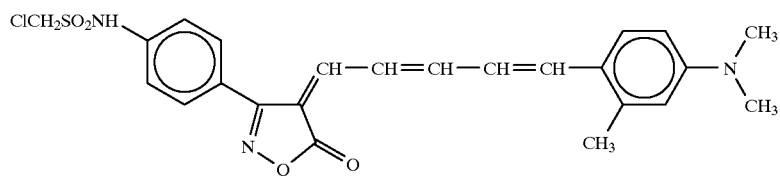
C-3
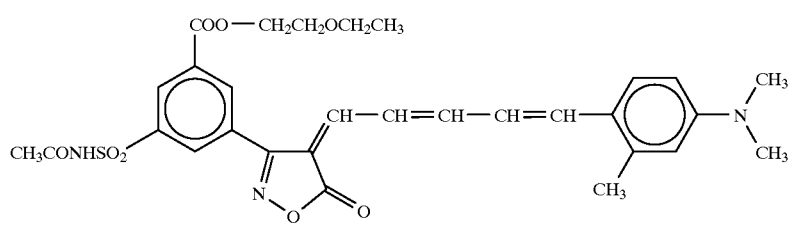
C-4
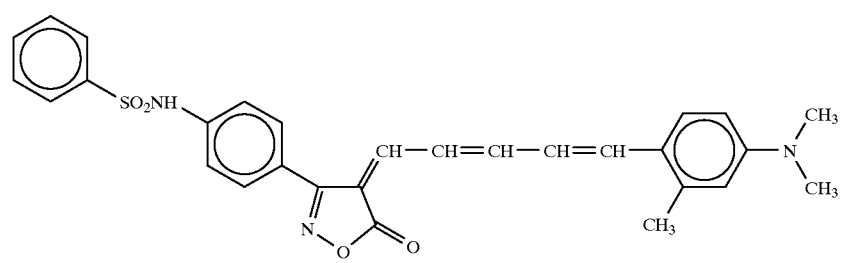
C-5

C-6
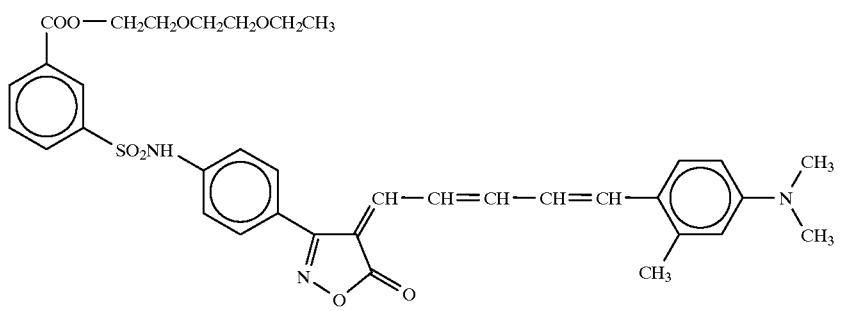
C-7
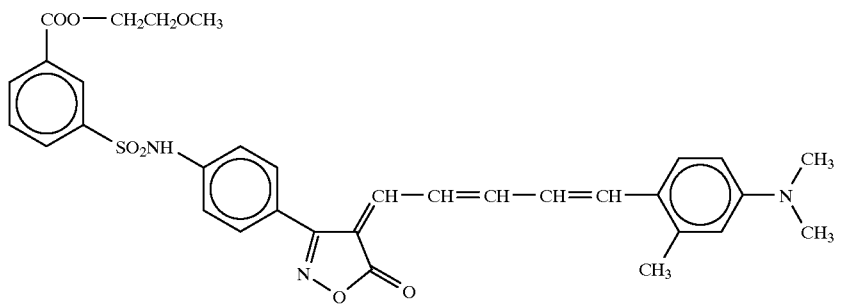
C-8
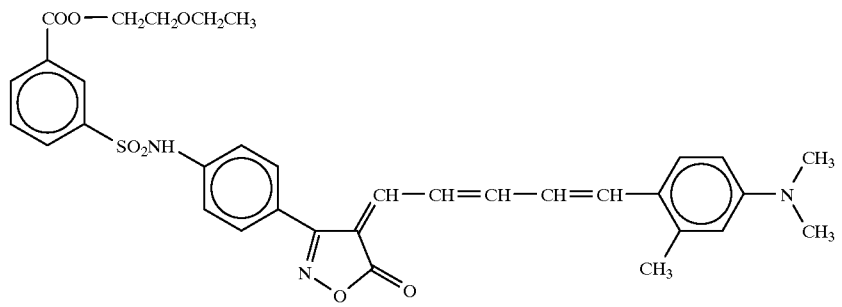
C-9
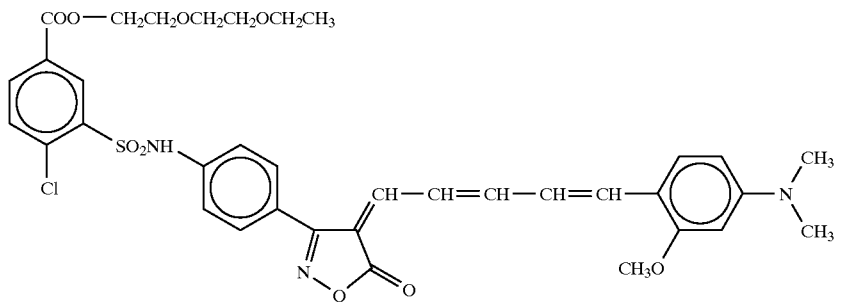

C-10
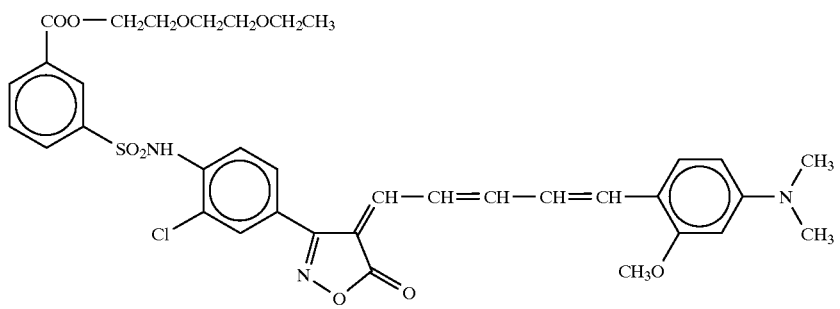
C-11
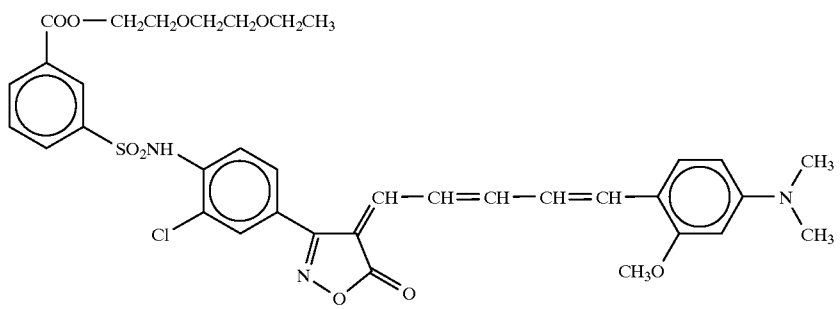
C-12
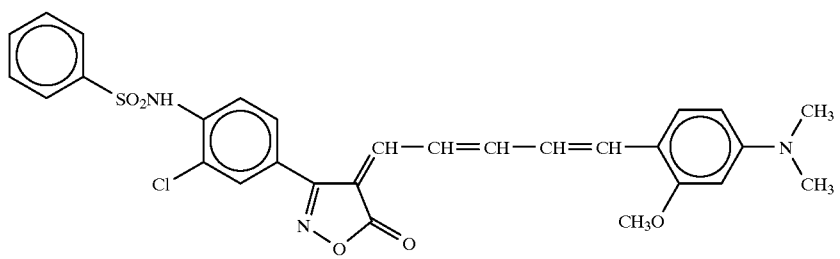
C-13
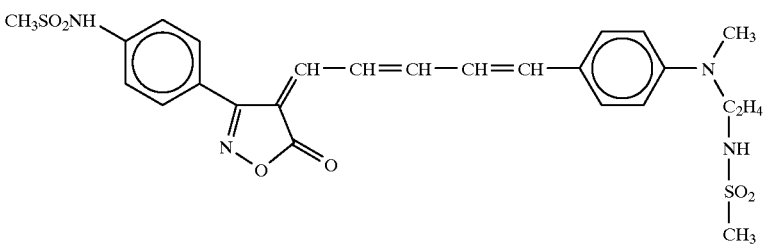
C-14
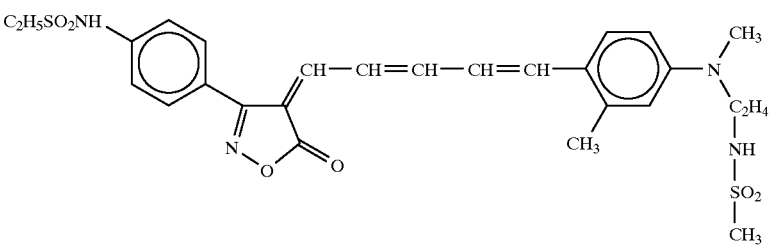

-continued
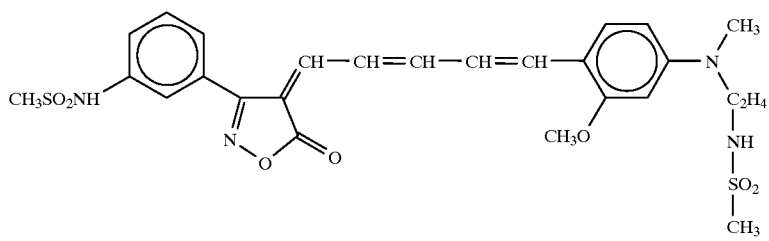
C-15
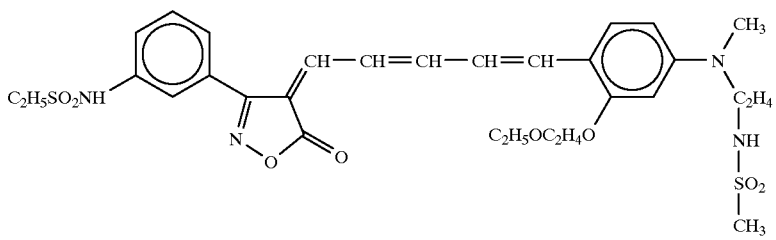
C-16
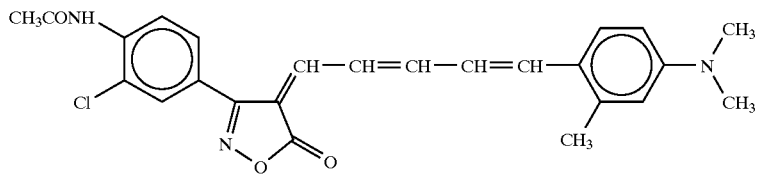
C-17
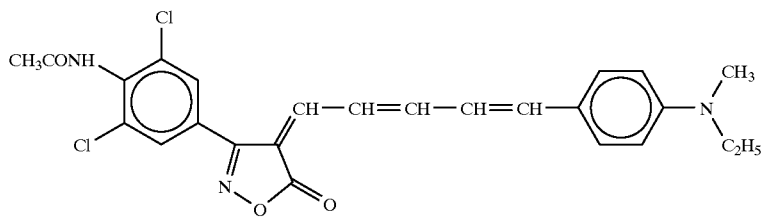
C-18
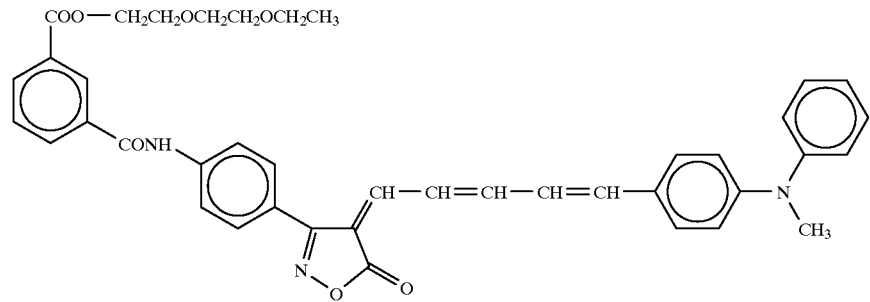
C-19

-continued
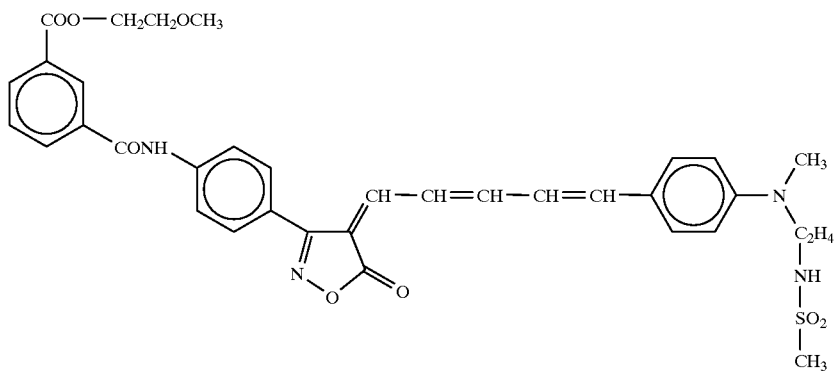
C-20
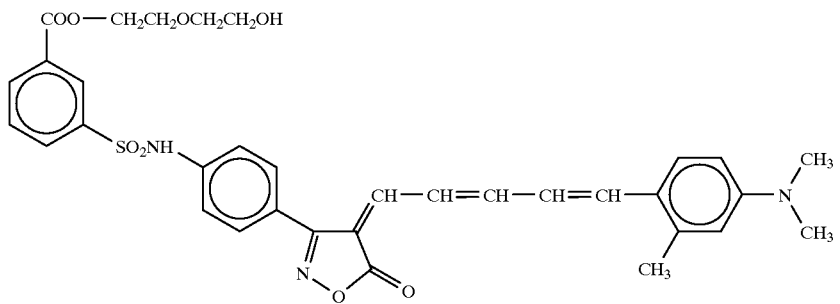
C-21
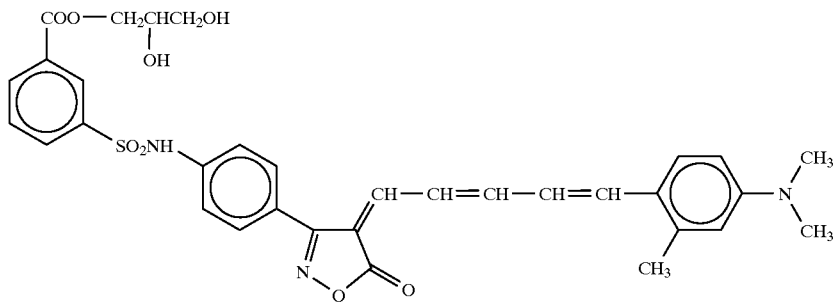
C-22
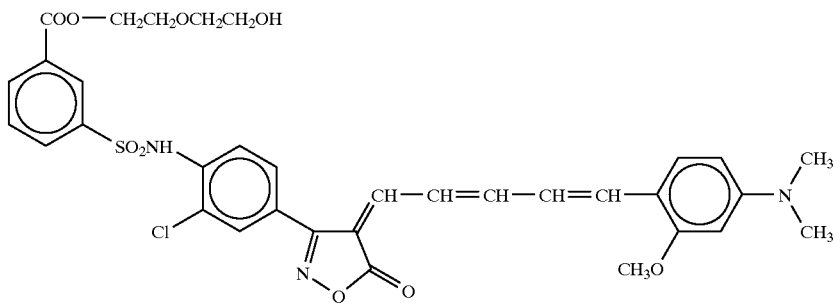
C-23

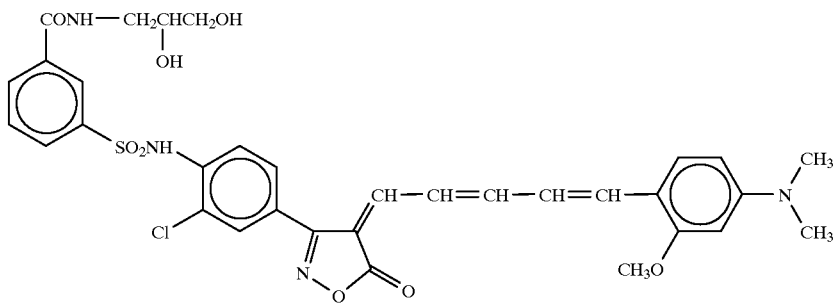
C-24
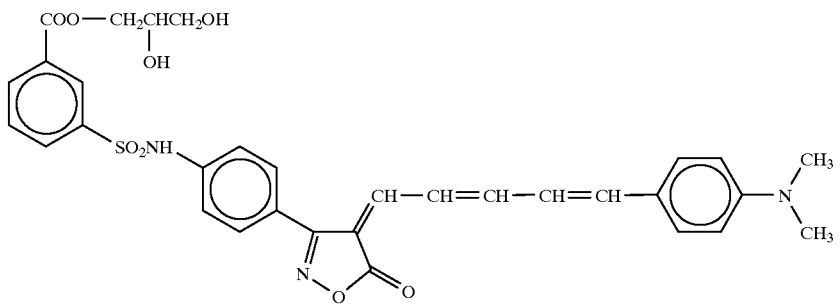
C-25
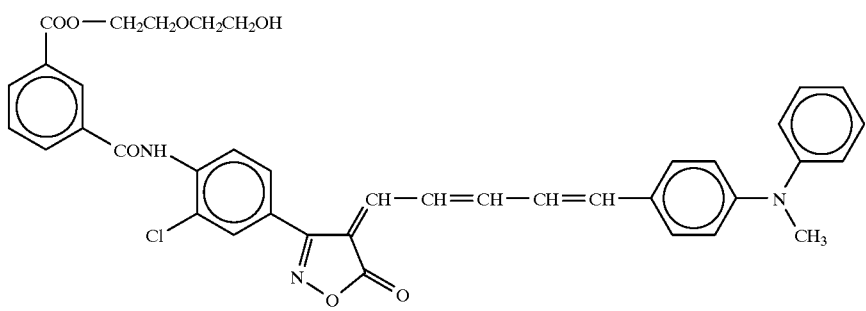
C-26
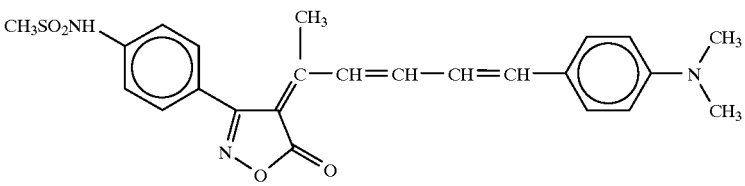
C-27
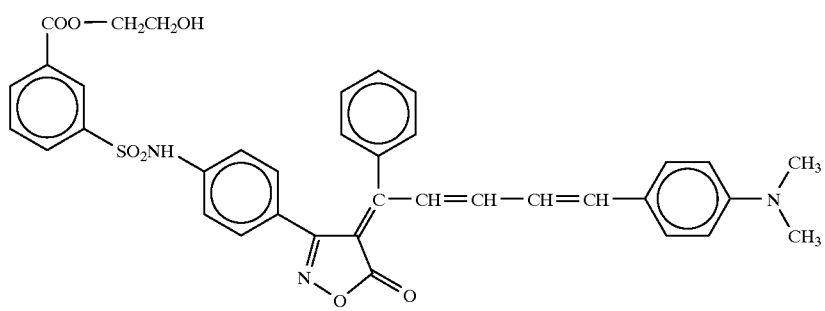
C-28

C-29
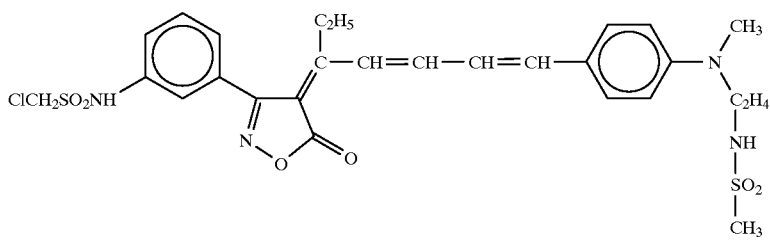

C-30
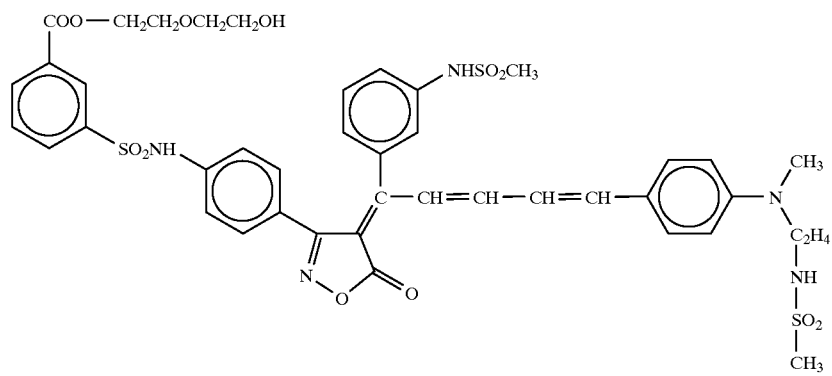

C-31
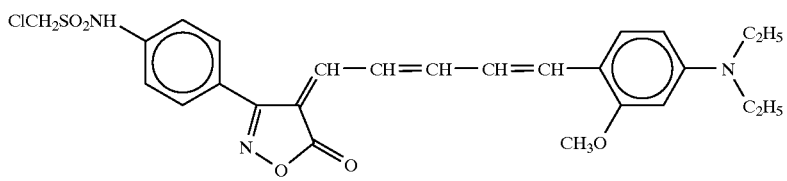

C-32
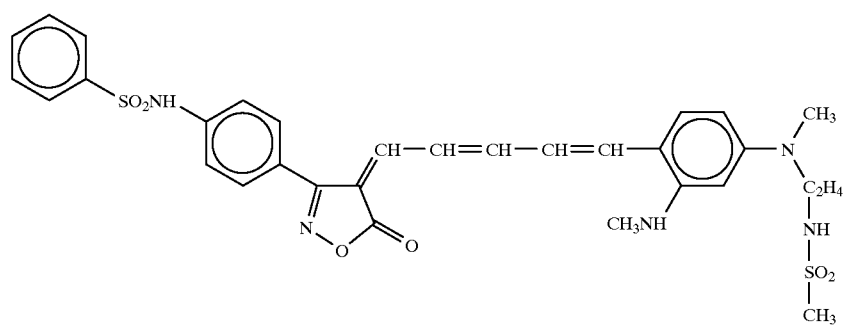

C-33
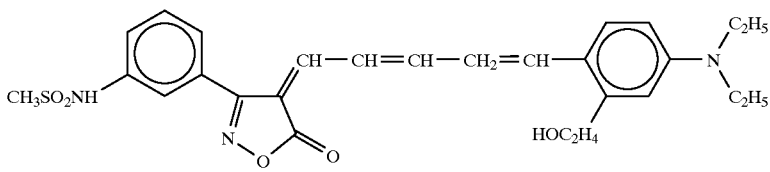

The arylidene compound represented by the formula (I) can be synthesized by mixing the isoxazolone represented by the formula (1) and the aldehyde represented by the formula (2) in an organic solvent (e.g., methanol, ethanol, acetonitrile, dimethylformamide, pyridine, acetic acid, acetic anhydride) at the room temperature or under heating and refluxing conditions. A catalyst (e.g., piperidine, glycine, β-alanine, p-toluenesulfonic acid, ammonium acetate) can be added to the synthesizing reaction.

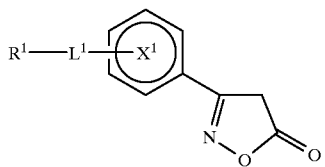

(1)

in which $L^1$, $R^1$ and $X^1$ have the same meanings as in the formula (I).

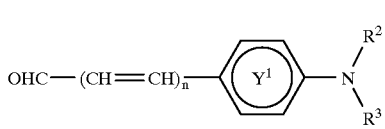

(2)

in which $R^2$, $R^3$ and $Y^1$ have the same meanings as in the formula (I), and n is 0, 1 or 2.

The arylidene compound can also be synthesized by reacting the dye represented by the formula (3) and the acid halide represented by the formula (4) with a base (e.g., pyridine, triethylamine, DBU) in an organic solvent at the room temperature.

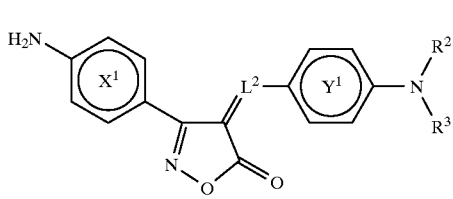

(3)

in which $L^2$, $R^2$, $R^3$, $X^1$ and $Y^1$ have the same meanings as in the formula (I).

(4)

in which $R^1$ has the same meanings as in the formula (I).

The arylidene compound represented by the formula (I) can be used as a dye in various technical fields. The arylidene compound is particularly effective in the case that the compound is used as a dye in a silver halide photographic material. The arylidene dye is added to a silver halide emulsion layer or a non-light-sensitive hydrophilic colloidal layer in such an amount that the optical density of the layer is in the range of 0.05 to 3.50. The amount is determined depending on use of the dye (for example, a filter dye, an antihalation dye).

According to use of the arylidene dye represented by the formula (I), the dye is added to a specific layer (a silver halide emulsion layer or a non-light-sensitive hydrophilic colloidal layer) of the silver halide photographic material. In more detail, the arylidene dye can be added to a coating solution of the layer.

The arylidene dye is preferably used in the form of molecular dispersion rather than solid particle dispersion. It is rather difficult to form molecular dispersion of the arylidene dye represented by the formula (I) in a photographic layer directly because the arylidene dye is rather hydrophobic while the photographic layer usually is hydrophilic. There are three methods of forming molecular dispersion of a relatively hydrophobic dye in a hydrophilic layer. The first method comprises forming molecular dispersion of the dye in oily droplets of an organic solvent, and dispersing the oily droplets in the layer. The second method comprises forming molecular dispersion of the dye in polymer particles, and dispersing the particles in the layer. The third method comprises dispersing the dye in the layer by using a surface active agent to form molecular dispersion in the layer. The second method is classified into three embodiments, namely an embodiment of using a water-insoluble polymer, another embodiment of using a latex and the other embodiment of using a hydrophilic polymer.

Accordingly, a molecular dispersion of the arylidene dye can be formed in a photographic layer by using (a) oily droplets of an organic solvent, (b) water-insoluble polymer particles, (c) polymer particles formed from a latex, (d) hydrophilic polymer particles, or (e) a surface active agent. The methods of (a) to (e) are described in more detail.

(a) The organic solvent is classified as miscible with water or not. An organic solvent not miscible with water is further classified into a high boiling point organic solvent having a boiling point of not lower than 150° C. (preferably not lower than 160° C.) and a low boiling point organic solvent having a boiling point in the range of 30 to 150° C.

Examples of the high boiling point organic solvents include alkyl phthalates (e.g., dibutyl phthalate, dioctyl phthalate), phosphoric esters (e.g., diphenyl phosphate, triphenyl phosphate, tricresyl phosphate, dioctyl butyl phosphate), citric esters (e.g., tributyl acetylcitrate), benzoic esters (e.g., octyl benzoate), alkylamides (e.g., diethyllaurylamide), trimesic esters (e.g., tributyl trimesate) and esters of other fatty acids (e.g., dibutoxyethyl succinate, diethyl azelate). The high boiling point organic solvents are described in U.S. Pat. No. 2,322,027.

Examples of the low boiling point organic solvents include lower alkyl esters of lower fatty acids (e.g., ethyl acetate, butyl acetate, ethyl propionate, β-ethoxyethyl acetate, methylcellosolve acetate), alcohols (e.g., secondary butanol) and ketones (e.g., methyl isobutyl ketone).

Examples of the organic solvents miscible with water include lower alcohols (e.g., methanol, ethanol).

The dye is dissolved in the organic solvent. The obtained solution is emulsified in a coating solution of a layer (hydrophilic colloid solution) of a silver halide photographic material to form a molecular dispersion in the layer.

The weight ratio of the dye to the organic solvent is preferably in the range of 10 to 0.1, and more preferably in the range of 4 to 0.25.

The average size of the oily droplets is preferably in the range of $10^{-3}$ to $10^3$ μm, and more preferably in the range of $10^{-3}$ to 10 μm.

(b) The dye is added to a water-insoluble (hydrophobic) polymer to form polymer particles containing the dye. The polymer particles are dispersed in a layer of a silver halide photographic material.

The water-insoluble polymers are described in Japanese Patent Provisional Publication Nos. 5(1993)-45789, 5(1993)-45794 and 5(1993)-158190.

The weight ratio of the dye to the water-insoluble polymer is preferably in the range of 10 to 0.1, and more preferably in the range of 4 to 0.25.

The average size of the polymer particles is preferably in the range of $10^{-3}$ to $10^3$ μm, and more preferably in the range of $10^{-3}$ to 10 μm.

(c) The dye is added to a latex to impregnate the polymer particles (or droplets) in the latex with the dye. The latex containing the dye is added to a coating solution of a layer to disperse the polymer particles in the layer.

The polymer of the latex preferably is polyurethane or polyolefin. The polyolefin is synthesized by polymerizing a vinyl monomer.

Examples of the vinyl monomers include acrylic acid, methacrylic acid, acrylic esters (e.g., methyl acrylate, ethyl acrylate, butyl acrylate, hexyl acrylate, octyl acrylate, dodecyl acrylate, glycidyl acrylate, hydroxyalkyl acrylate, sulfoalkyl acrylate), α-substituted acrylic esters (e.g., methyl methacrylate, butyl methacrylate, octyl methacrylate, glycidyl methacrylate, hydroxyalkyl methacrylate, sulfoalkyl methacrylate), acrylamides (e.g., butylacrylamide, hexylacrylamide), α-substituted acrylamides (e.g., butylmethacrylamide, hexylmethacrylamide), vinyl esters (e.g., vinyl acetate, vinyl butyrate), vinyl halides (e.g., vinyl chloride), vinylidene halides (e.g., vinylidene chloride), vinyl ethers (e.g., vinyl methyl ether, vinyl octyl ether), styrene, α-substituted styrenes (e.g., α-methylstyrene), benzene-substituted styrene (e.g., hydroxystyrene, chlorostyrene, methylstyrene, styrenesulfonic acid), ethylene, propylene, butylene, butadiene, acrylonitrile and itaconic acid.

A copolymer made from two or more monomers can be used in the latex.

The latex and the preparation thereof are described in Japanese Patent Publication No. 51(1976)-39853, Japanese Patent Provisional Publication Nos. 51(1976)-59943, 53(1978)-137131, 54(1979)-32552, 54(1979)-107941, 55(1980)-133465, 56(1981)-19043, 56(1981)-19047, 56(1981)-126830 and 58(1983)-149038.

The weight ratio of the dye to the latex is preferably in the range of 10 to 0.1, and more preferably in the range of 4 to 0.25.

The average size of the polymer particles formed from the latex is preferably in the range of $10^{-3}$ to $10^3$ μm, and more preferably in the range of $10^{-3}$ to 10 μm.

(d) The dye is added to a hydrophilic polymer to form polymer particles containing the dye. The polymer particles are dispersed in a layer of a silver halide photographic material.

The hydrophilic polymers are described in U.S. Pat. No. 3,619,195 and German Patent No. 1,957,467.

The weight ratio of the dye to the hydrophilic polymer is preferably in the range of 10 to 0.1, and more preferably in the range of 4 to 0.25.

The average size of the polymer particles is preferably in the range of $10^{-3}$ to $10^3$ μm, and more preferably in the range of $10^{-3}$ to 10 μm.

(e) The surface active agent for dispersing the dye preferably is an oligomer or a polymer. The polymer surface active agent is described in Japanese Patent Provisional Publication No. 60(1985)-158437 (pages 2 to 8).

The hydrophilic group of the surface active agent is classified as nonionic, anionic, amphoteric and cationic. Examples of the nonionic surface active agents include steroid compounds (e.g., saponin), alkylene oxide derivatives (e.g., polyethylene glycol, condensation products of polyethylene glycol with polypropylene glycol, alkyl ethers of polyethylene glycol, alkyl aryl ethers of polyethylene glycol, polyethylene glycol esters, polyethylene glycol sorbitan esters, alkyl amines or amides of polyalkylene glycol, polyethylene oxide additives of silicone), glycidol derivatives (e.g., polyglyceride of alkenylsuccinic acid, polyglyceride of alkylphenol) and fatty acid esters of polyhydric alcohol. Examples of the anionic surface active agents include alkylcarboxylic acids, alkylsulfonic acids, alkylbenzensulfonic acids, alkylnaphthalenesulfonic acids, alkylsulfuric esters, alkylphosphoric esters, N-acyl-N-alkyltaurines, sulfosuccinic esters, sulfoalkyl polyoxyethylene alkyl phenyl ethers and polyoxyethylene alkylphosphoric esters. Examples of the amphoteric surface active agents include amino acids, aninoalkylsulfonic acids, aminoalkylsulfuric acids, aminoalkylphosphoric acids, alkylbetaines and amine oxides. Examples of the cationic surface active agents include alkylamine salts, aliphatic or aromatic quaternary ammonium salts, heterocyclic quarternary ammonium (e.g., pyridinium, imidazolium) salts, aliphatic or heterocyclic phosphonium salts and aliphatic or heterocyclic sulfonium salts.

The coating solution of a silver halide photographic material contains a hydrophilic colloid (usually gelatin). The surface active agent has a function of dispersing the dye in the hydrophilic colloid. A hydrosol of a hydrophilic polymer (described in Japanese Patent Publication No. 51(1976)-39835) can be added to the hydrophilic colloid.

Two or more methods of (a) to (e) can be used in combination. For example, the polymer of (b) or (d) can be added to the oil droplets of (a). In the combination, the polymer of (b) or (d) is preferably soluble in the organic solvent of (a).

The methods of (a) to (d) are preferred, the methods of (a) and (c) are more preferred, and the method of (a) is most preferred.

The silver halide emulsion layer and the non-light-sensitive hydrophilic colloidal layer is prepared by using a hydrophilic colloid. Gelatin is the representative hydrophilic colloid.

Silver halide emulsions preferably used in the photographic material include a silver bromide emulsion, a silver iodobromide emulsion, a silver iodochlorobromide emulsion, a silver chlorobromide emulsion and a silver chloride emulsion.

There is no specific limitation about the grain size of silver halide. A photographic material can contain fine grains of not more than 0.1 μm. A photographic material can also contain large grains of about 10 μm (based on the projected area).

A silver halide emulsion preferably has such a uniform grain size distribution that the weight amount of silver halide grains having a grain size within the range of ±20% of the average grain size is not less than 60 wt. % (more preferably not less than 80 wt. %) of the total silver halide grains. Monodispersed emulsions having a uniform grain size distribution are described in U.S. Pat. Nos. 3,574,628, 3,655, 394 and British Patent No. 1,413,748.

The silver halide grains can be in the form of a regular (such as cubic, octahedral, tetradecahedral) crystal or an irregular (such as spherical, tabular) crystal. The grain can have a crystal defect (e.g., twinned face). The silver halide grains can also be in the form of a complex crystal.

A tabular silver halide emulsion preferably contains tabular grains having an aspect ratio (diameter of a circle corresponding to the projected area of a silver halide grain per thickness of the grain) of not less than 3 in an amount of not less than 50% based on the projected area. The tabular grain and the preparation thereof are described in Gutoff, Photographic Science and Engineering, volume 14, pages 248 to 257 (1970), U.S. Pat. Nos. 4,434,226, 4,414,310, 4,433,048, 4,439,520 and British Patent No. 2,112,157.

A silver halide emulsion can be prepared according to known processes, which are described in Research Disclosure (RD) No. 17,643 (December, 1978), pages 22 to 23 (Emulsion preparation and types), No. 18,716 (November, 1979), page 648, No. 307,105 (November, 1989), pages 863 to 865, P. Glafkides, Chimie et Physique Photographique (Paul Montel, 1967), G. F. Duffin, Photographic Emulsion Chemistry (The Focal Press, 1966), and V. L. Zelikman et al., Making and Coating Photographic Emulsion (The Focal Press, 1964).

The grain size of a silver halide emulsion can be adjusted by conducting nuclear formation and grain growth according to a double jet method while controlling pAg. The pAg is so controlled as to keep supersaturation and not to form a nuclear reformation.

An emulsion can also be prepared by a process of adding potassium iodide gelatino aqueous solution and ammonium silver nitrate aqueous solution to gelatino aqueous solution containing silver halide grains while changing the addition rate according to a function of time (described in Japanese Patent Provisional Publication No. 54(1979)-48521). A high monodispersed emulsion can be prepared by adjusting the addition rate according to a function of time, pH, pAg or the temperature. The conditions are described in detail in Photographic Science and Engineering, volume 6, pages 159 to 165 (1962), Journal of Photographic Science, volume 12, pages 242 to 252 (1964), U.S. Pat. No. 3,655,394 and British Patent No. 1,413,748.

Silver halide grains can have a uniform halide composition in its crystal structure. Silver halide grains can also be made of internal and external phases, which differ in halide composition. The grains made of two or more phases can have a layered structure. The grains made of two or more phases are described in British Patent No. 1,027,146 and U.S. Pat. Nos. 3,505,068, 4,444,877. Silver halide grains can be conjugated with silver halide of another halide composition by an epitaxial conjugation. Further, grains can be conjugated with a compound other than silver halide, such as silver rhodanide and lead oxide.

Silver halide grains preferably have a distribution or a structure about halide composition. For example, the grains preferably has a core-shell structure or a double structure, which differs in halide composition (described in Japanese Patent Publication No. 43(1968)-13162, Japanese Patent Provisional Publication Nos. 60(1985)-222845, 61(1986)-75337 and 61(1986)-215540).

Further, the grains can have a triple or more structure (described in Japanese Patent Publication No. 60(1985)-222844). Furthermore, on the surface of grains of a core-shell structure, a thin layer of silver halide of anther halide composition can be formed.

A structure about halide composition can be formed not only by forming the layered structure mentioned above but also by fusing another silver halide with the grains. Fused grains are described in Japanese Patent Publication No. 58(1983)-24772, Japanese Patent Provisional Publication Nos. 58(1983)-108526, 59(1984)-16254, 59(1984)-133540 and European Patent Publication No. 199290A2. The host crystals and the other crystals (i.e., the guest crystals) differ in halide composition. To form a crystal of the fused structure, the guest crystals are fused at the edge, the corner or the face of the host crystal. Such fused crystals can be prepared whether the host crystal has homogeneous halogen composition or not. For example, even if the host crystal has a core-shell type structure, the fused crystals can be further formed. The fused crystals may consist of a combination of a silver halide and a silver salt that does not have the rock salt structure (e.g., silver rhodanate, silver carbonate) as well as a combination of silver halides.

For example, silver iodobromide grain of core-shell type may contain such iodide distribution that silver iodide content in the core is higher than that in the shell. Further, the grain may have such a structure that silver iodide content in the shell is higher than that in the core. In the case of silver iodobromide grains of fused crystals, the silver iodide content in the host crystals may be higher than that in the guest crystal. The content in the guest crystal may also be higher than that in the host crystal.

In the above-described grains consisting of two or more portions in which compositions of silver halide are different each other, the portions can be distinguished by a clear border. The border can also be vague. Mixed crystals of adjoining parts have such a vague border. Further, the composition may be gradually changed between the portions.

The silver halide emulsion may be so treated that the grains be rounded (as is described in European Patent Nos. 0096727B1 and 0064412B1). Further, the surface of the grains can be modified (as is described in German Patent No. 2306447C2 and Japanese Patent Provisional Publication No. 60(1985)-221320).

A silver halide emulsion of surface latent image type is preferred. An emulsion of internal latent image type can also be used, if developers and developing conditions are appropriately selected (as is described in Japanese Patent Provisional Publication No. 59(1084)-133542). Further, an emulsion of shallow-internal latent image type (such emulsion contains the grains covered with thin shell) can optionally be used.

A silver halide solvent can be used to accelerate ripening a silver halide emulsion. Further, it has been known that the ripening is accelerated in the case that an excess amount of halide ion is present in a reaction vessel. Accordingly, a solution of halide salt in place of the silver halide solvent can be added to the reaction vessel to accelerate the ripening. A ripening agent other than the silver halide solvent can be used. The whole amount of the ripening agent can be added to a dispersing medium in a reaction vessel before adding a silver salt and a halide salt. Further, the ripening agent can be incorporated into the reaction vessel with one or more of the halide salt, the silver salt and a protective colloid. Furthermore, the ripening agent can be incorporated into the reaction vessel simultaneously but independently of the addition of the halide salt and the silver salt.

Examples of the ripening agents other than halide ion include ammonia, amines, thiocyanate salts (e.g., ammonium thiocyanate salt, alkaline metal thiocyanate salt, particularly sodium or potassium thiocyanate).

A silver halide emulsion is usually chemically sensitized (chalcogen sensitization, noble metal sensitization or reduction sensitization).

In the case that silver halide grains are doped with a polyvalent metal ion in an amount of not less than $1 \times 10^{-4}$ mol based on 1 mol of silver halide, the doping effect is remarkable after the emulsion is chemically sensitized. If the emulsion is not ripened, the doping effect is scarcely observed. The chemical sensitization can be applied to any portions of grains. The sensitized portion is determined depending on the composition, the structure or the shape of the grains or the use of the emulsion. A chemically sensitized speck is formed inside the grains, in a shallow internal portion of the grains or on the surface of the grains. The doping effect is remarkable in the case that the chemically sensitized speck is formed near the surface of the grains. Accordingly, the doping of a polyvalent metal ion is effective in a surface latent image type emulsion rather than an internal latent image type emulsion.

A chemical sensitization can be conducted by using an active gelatin, as is described in T. H. James, The Theory of the Photographic Process, 4th edition, Macmillan, 1977, pages 67 to 76. The chemical sensitization is preferably conducted at pAg of 5 to 10, pH of 5 to 8 and a temperature of 30 to 80° C., as is described in Research Disclosure Nos. 10210 (April 1974), 13452 (June 1975), U.S. Pat. Nos. 2,642,361, 3,297,446, 3,772,031, 3,857,711, 3,901,714, 3,904,415, 4,266,018 and British Patent No. 1,315,755.

The chalcogen sensitization is conducted by using a sulfur, selenium or tellurium compound as a sensitizer. The noble metal sensitization is conducted by using a gold, platinum or iridium compound as a sensitizer. Two or more sensitizers can be used in combination. For example, a noble metal sensitization can be conducted by using a gold compound in combination with a thiocyanate compound. Examples of the sulfur sensitizers include hypo, thiourea compounds and rhodanine compounds. The sulfur sensitizers are described in U.S. Pat. Nos. 3,857,711, 4,054,457 and 4,266,018.

The chemical sensitization can be conducted in the presence of a chemical sensitizing aid, which has a function of inhibiting a fog and increasing a sensitivity at the stage of the chemical sensitization. Examples of the chemical sensitizing aids include azaindenes, azapyridazines and azapyrimidines. The chemical sensitizing aids (or chemical sensitization improving agents) are described in U.S. Pat. Nos. 2,131,038, 3,411,914, 3,554,757, Japanese Patent Provisional Publication No. 58(1983)-126526 and G. F. Duffin, Photographic Emulsion Chemistry (The Focal Press, 1966), pages 138 to 143.

The present invention is effective in each of a black and white photographic material and a color photographic material. The color photographic materials include a color paper, a color photographic film and a color reversal film. The black and white photographic materials include a X-ray film, a black and white photographic film and a lithographic printing film.

A color photographic material usually has a multi-layered structure, which comprises two or more silver halide emulsion layers and two or more non-light-sensitive hydrophilic colloidal layers. The non-light-sensitive hydrophilic colloidal layers include a protective layer provided on an emulsion layer, an intermediate layer provided between emulsion layers, an undercoating layer provided between an emulsion layer and a support and a backing layer provided on the backing surface (the surface on which emulsion layers are not provided) of the support. The dye is added to one of the layers depending on the function of the dye. In the case that the dye functions as a filter, the dye is added to a protective layer or an intermediate layer. In the case that the dye functions as an antihalation dye, the dye is added to an undercoating layer or a backing layer. In the case that the dye functions as an antiirradiation dye, the dye is added to a silver halide emulsion layer.

There is no specific limitation about additives of a silver halide photographic material. The additives are described in Research Disclosure, volume 176, item 17643 (RD-17643) and volume 187, item 18716 (RD-18716).

The descriptions in the Research Disclosures are shown below.

| Additives | RD-17643 | RD-18716 |
|---|---|---|
| Chemical sensitizer | page 23 | page 648, right column |
| Sensitivity increasing agent | | page 648, right column |
| Spectral sensitizer and supersensitizer | pages 23–24 | page 648, right column to page 649, right column |
| Brightening agent | page 24 | |
| Anti-fogging agent and stabilizer | pages 24–25 | page 649, right column |
| Light-absorber, filter dye and UV absorber | pages 25–26 | page 649, right column to page 650, left column |
| Anti-stain agent | page 25 | page 650, left column to right column |
| Color-image stabilizer | page 25 | |
| Hardening agent | page 26 | page 651, left column |
| Binder | page 26 | page 651, left column |
| Plasticizer and slipping agent | page 27 | page 650, right column |
| Coating aid and surface active agent | pages 26–27 | page 650, right column |
| Antistatic agent | page 27 | page 650, right column |

The dye can be added to a heat developable silver halide photographic material, which is described in U.S. Pat. No. 4,500,626, European Patent No. 210660A2, Japanese Patent Provisional Publication Nos. 59(1984)-218443, 60(1985)-133449 and 61(1986)-238056.

The present invention is particularly effective in a silver halide photographic material for a conventional wet development.

A wet development using an automatic developing machine is described in Japanese Patent Provisional Publication Nos. 3(1991)-13937 (pages 20 to 21, 25, 30 to 33, 40, 45 to 46 and 52 to 53), 3(1991)-171136 (pages 18 to 19) and 6(1994)-43583 (page 27).

After a color photographic material is imagewise exposed to light, the material is subjected to a development process, a bleach fixing process or a fixing process and a washing process or a stabilizing process.

A color photographic material is usually treated with a conventional color development, which is described at pages 28 to 29 in RD-17643 and at the left to right columns of page 651 of RD-18716.

After the color development, the color photographic material is usually treated with a bleach-fix or fixing process and a washing or stabilizing process.

The replenishing amount of a developing solution or a fixing solution is preferably in the range of 25 to 200 ml, more preferably in the range of 30 to 180 ml, and most preferably in the range of 60 to 150 ml, based on 1 $m^2$ of a photographic material.

The development process is preferably completed for not longer than 5 minutes, more preferably for 5 to 60 seconds, and most preferably for 5 to 30 seconds.

The washing process is generally carried out according to a countercurrent method using two or more washing tanks to save water. A multistage countercurrent stabilizing process (described in Japanese Patent Provisional Publication No. 57(1982)-8543) can be carried out instead of the washing process.

A color developing solution for a development of a color photographic material preferably is an alkaline solution of an aromatic primary amine color developer. An aminophenol compound can be used as the color developer. However, p-phenylenediamine compound is preferably used as the color developer. Examples of the p-phenylenediamine compounds include 3-methyl-4-amino-N,N-diethylaniline, 3-methyl-4-amino-N-ethyl-N-β-hydroxyethylaniline, 3-methyl-4-amino-N-ethyl-β-methanesulfonamidoethylaniline, 3-methyl-4-amino-N-ethyl-p-methoxyethylaniline, and sulfate salts, chloride salts or p-toluenesulfonate salts thereof.

According to a reversal method, a color development is conducted after a black and white development. A black and white developing solution contains a black and white developer such as dihydroxybenzenes (e.g., hydroquinone), 3-pyrazolidones (e.g., 1-phenyl-3-pyrazolidone) and aminophenols (e.g., N-methyl-p-aminophenol).

The color developing solution or the black and white developing solution has a pH value usually in the range of 9 to 12.

After the development, a silver halide emulsion layer is usually subjected to a bleaching process. The bleaching process can be conducted simultaneously with a fixing process (as a bleach fixing process). The bleaching process and the fixing process can separately be conducted. After the bleaching process, a bleach fixing process can be conducted to accelerate the process. A bleaching solution or a bleach fixing solution preferably contains a complex salt of iron(III) with aminopolycarboxylic acid. The solution containing the complex has a pH value usually in the range of 5.5 to 8. The process can be conducted at a lower pH value to accelerate the process.

A bleaching solution, a bleach fixing solution or a pre-bath thereof can contain a bleaching accelerator, which preferably is a compound having a mercapto group or disulfide group. A silver halide photographic material can contain the bleaching accelerator.

A typical example of a fixing agent is a thiosulfate salt.

After a desilvering process, a silver halide photographic material is usually subjected to a washing process or a stabilizing process. The amount of water used in the washing process depends on various conditions, such as the characteristic and use of a photographic material, the temperature of water, the number of tanks or a replenishing method (counter current or not). The relation between the number of the tanks and the amount of water in a multistage counter-current method is described in Journal of the Society of Motion Picture and Television Engineering, volume 64 pages 248 to 253 (May 1995).

SYNTHESIS EXAMPLE 1

Synthesis of compound B-6

With 10 ml of N,N-dimethylacetamide (DMAC), 1.24 g of the following compound a and 1.5 g of the following compound b were mixed. To the mixture, 0.0365 ml of pyridine was dropwise added. The mixture was reacted at the room temperature for 2 hours. The reaction mixture was poured into 300 ml of distilled water. Precipitated crystals were filtered off to obtain 2.3 g of the compound B-6. The melting point was 115° C., and λ max was 511.0 nm (in ethyl acetate).

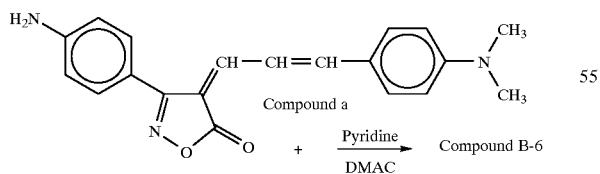

Compound a

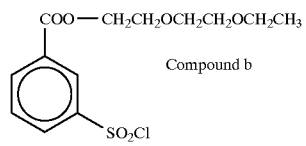

Compound b

SYNTHESIS EXAMPLE 2

Synthesis of compound B-7

With 23 ml of ethanol, 2 g of the following compound c and 760 mg of the following compound d were mixed. The mixture was refluxed for 2 hour while heating. After the reaction mixture was cooled, the mixture was poured into 300 ml of distilled water. Precipitated crystals were filtered off to obtain 2.5 g of the compound B-7. The melting point was 138° C., and λ max was 510.9 nm (in ethyl acetate).

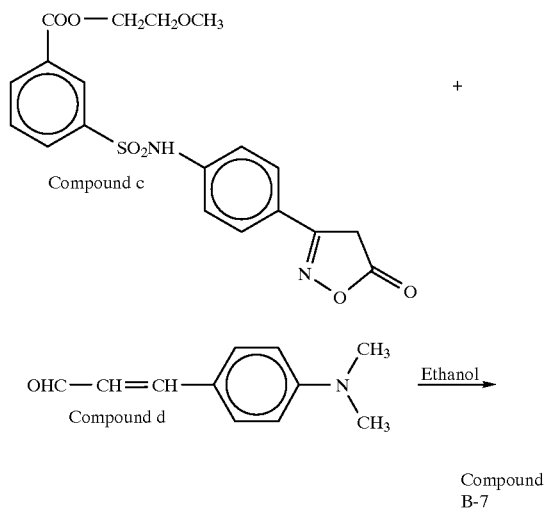

SYNTHESIS EXAMPLE 3

Synthesis of Compound B-26

The compound B-26 was synthesized in the same manner as in the Synthesis Example 1, except that the compound a and the following compound e were used. The melting point was 154° C., and λ max was 509.0 nm (in ethyl acetate).

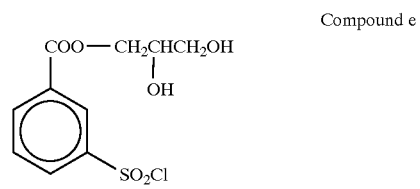

SYNTHESIS EXAMPLE 4

Synthesis of Compound B-22

The compound B-22 was synthesized in the same manner as in the Synthesis Example 1, except that the following compound f and the compound e were used. The melting point was 154° C., and λ max was 512.0 nm (in ethyl acetate).

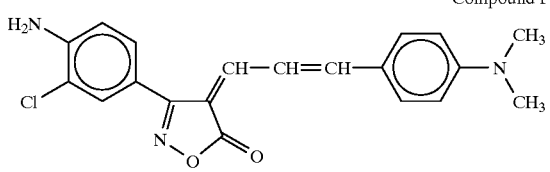

Compound f

SYNTHESIS EXAMPLE 5

Synthesis of Compound B-9

The compound B-9 was synthesized in the same manner as in the Synthesis Example 1, except that the compound f and the following compound g were used. The melting point was 123° C., and λ max was 510.2 nm (in ethyl acetate).

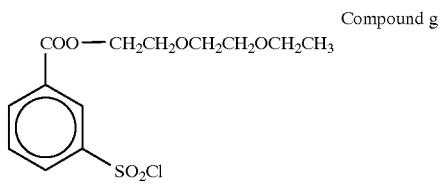

Compound g

SYNTHESIS EXAMPLE 6

Synthesis of Compound B-23

The compound B-23 was synthesized in the same manner as in the Synthesis Example 1, except that the compound f and the following compound h were used. The melting point was 134° C., and λ max was 510.4 nm (in ethyl acetate).

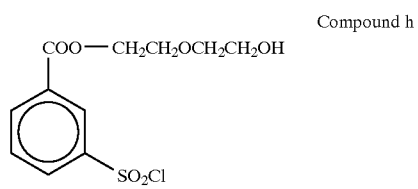

Compound h

SYNTHESIS EXAMPLE 7

Synthesis of Compound B-24

The compound B-24 was synthesized in the same manner as in the Synthesis Example 1, except that the compound f and the following compound i were used. The melting point was 172° C., and λ max was 513.0 nm (in ethyl acetate).

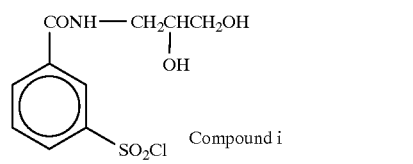

Compound i

EXAMPLE 1

The following layers were simultaneously coated on an undercoating layer of a cellulose triacetate film support to prepare a multi-layered color photographic material (sample No. 101).

The coating amounts (g per m$^2$) of the components of the layers are shown below (except that the amounts of the sensitizing dye mean mole per 1 mole of silver halide contained in the same layer).

| First layer (antihalation layer) | |
|---|---|
| Black colloidal silver (coating amount of silver) | 0.18 |
| Gelatin | 1.40 |
| Second layer (intermediate layer) | |
| 2,5-Di-t-pentadecylhydroquinone | 0.18 |
| EX-1 | 0.18 |
| EX-3 | 0.020 |
| EX-12 | $2.0 \times 10^{-3}$ |
| U-1 | 0.060 |
| U-2 | 0.080 |
| U-3 | 0.10 |
| Tricresyl phosphate | 0.10 |
| Di-n-butyl phthalate | 0.020 |
| Gelatin | 1.04 |
| Third layer (first red sensitive emulsion layer) | |
| Emulsion A (coating amount of silver) | 0.25 |
| Emulsion B (coating amount of silver) | 0.25 |
| Sensitizing dye I | $6.9 \times 10^{-5}$ |
| Sensitizing dye II | $1.8 \times 10^{-5}$ |
| Sensitizing dye III | $3.1 \times 10^{-4}$ |
| EX-2 | 0.17 |
| EX-10 | 0.020 |
| EX-14 | 0.17 |
| U-1 | 0.070 |
| U-2 | 0.050 |
| U-3 | 0.070 |
| Tricresyl phosphate | 0.060 |
| Gelatin | 0.87 |
| Fourth layer (Second red sensitive emulsion layer) | |
| Emulsion G (coating amount of silver) | 1.00 |
| Sensitizing dye I | $5.1 \times 10^{-5}$ |
| Sensitizing dye II | $1.4 \times 10^{-5}$ |
| Sensitizing dye III | $2.3 \times 10^{-4}$ |
| EX-2 | 0.20 |
| EX-3 | 0.050 |
| EX-10 | 0.015 |
| EX-14 | 0.20 |
| EX-15 | 0.050 |
| U-1 | 0.070 |
| U-2 | 0.050 |
| U-3 | 0.070 |
| Gelatin | 1.30 |
| Fifth layer (third red sensitive emulsion layer) | |
| Emulsion D (coating amount of silver) | 1.60 |
| Sensitizing dye I | $5.4 \times 10^{-5}$ |
| Sensitizing dye II | $1.4 \times 10^{-5}$ |
| Sensitizing dye III | $2.4 \times 10^{-4}$ |
| EX-2 | 0.097 |
| EX-3 | 0.010 |
| EX-10 | 0.080 |
| Tricresyl phosphate | 0.22 |
| Di-n-butyl phthalate | 0.10 |
| Gelatin | 1.63 |
| Sixth layer (intermediate layer) | |
| EX-5 | 0.040 |
| Tricresyl phosphate | 0.020 |
| Gelatin | 0.80 |
| Seventh layer (first green sensitive emulsion layer) | |
| Emulsion A (coating amount of silver) | 0.15 |
| Emulsion B (coating amount of silver) | 0.15 |
| Sensitizing dye IV | $3.0 \times 10^{-5}$ |
| Sensitizing dye V | $1.0 \times 10^{-4}$ |
| Sensitizing dye VI | $3.8 \times 10^{-4}$ |
| EX-1 | 0.021 |
| EX-6 | 0.26 |
| EX-7 | 0.030 |
| EX-8 | 0.025 |
| Tricresyl phosphate | 0.10 |
| HBS | 0.010 |

| First layer (antihalation layer) | |
|---|---|
| Gelatin | 0.63 |
| Eighth layer (second green sensitive emulsion layer) | |
| Emulsion C (coating amount of silver) | 0.45 |
| Sensitizing dye IV | $2.1 \times 10^{-5}$ |
| Sensitizing dye V | $7.0 \times 10^{-5}$ |
| Sensitizing dye VI | $2.6 \times 10^{-4}$ |
| EX-6 | 0.094 |
| EX-7 | 0.026 |
| EX-8 | 0.018 |
| Tricresyl phosphate | 0.16 |
| HBS | $8.0 \times 10^{-3}$ |
| Gelatin | 0.50 |
| Ninth layer (third green sensitive emulsion layer) | |
| Emulsion E (coating amount of silver) | 1.20 |
| Sensitizing dye IV | $3.5 \times 10^{-5}$ |
| Sensitizing dye V | $8.0 \times 10^{-5}$ |
| Sensitizing dye VI | $3.0 \times 10^{-4}$ |
| EX-1 | 0.013 |
| EX-11 | 0.065 |
| EX-13 | 0.019 |
| Tricresyl phosphate | 0.25 |
| Di-n-butyl phthalate | 0.10 |
| Gelatin | 1.54 |
| Tenth layer (yellow filter layer) | |
| Yellow colloidal silver (coating amount of silver) | 0.050 |
| EX-5 | 0.12 |
| Tricresyl phosphate | 0.08 |
| Gelatin | 0.95 |
| Eleventh layer (first blue sensitive emulsion layer) | |
| Emulsion A (coating amount of silver) | 0.080 |
| Emulsion B (coating amount of silver) | 0.070 |
| Emulsion F (coating amount of silver) | 0.070 |
| Sensitizing dye VII | $3.5 \times 10^{-4}$ |
| EX-8 | 0.042 |
| EX-9 | 0.72 |
| Tricresyl phosphate | 0.28 |
| Gelatin | 1.10 |
| Twelfth layer (second blue sensitive emulsion layer) | |
| Emulsion G (coating amount of silver) | 0.45 |
| Sensitizing dye VII | $2.1 \times 10^{-4}$ |
| EX-9 | 0.15 |
| EX-10 | $7.0 \times 10^{-3}$ |
| Tricresyl phosphate | 0.050 |
| Gelatin | 0.78 |
| Thirteenth layer (third blue sensitive emulsion layer) | |
| Emulsion H (coating amount of silver) | 0.77 |
| Sensitizing dye VII | $2.2 \times 10^{-4}$ |
| Ex-9 | 0.20 |

| First layer (antihalation layer) | |
|---|---|
| Tricresyl phosphate | 0.070 |
| Gelatin | 0.69 |
| Fourteenth layer (first protective layer) | |
| Emulsion I (coating amount of silver) | 0.20 |
| U-4 | 0.11 |
| U-5 | 0.17 |
| Tricresyl phosphate | $5.0 \times 10^{-2}$ |
| Gelatin | 1.00 |
| Fifteenth layer (second protective layer) | |
| H-1 | 0.40 |
| P-1 (diameter: 1.7 μm) | $5.0 \times 10^{-2}$ |
| P-2 (diameter: 1.7 μm) | 0.10 |
| P-3 | 0.10 |
| S-1 | 0.20 |
| Gelatin | 1.20 |

The emulsions are shown below. The emulsions A to H contain silver halide grains of a double structure of core/shell type. Only the emulsion I contains uniform silver halide grains.

| Emulsion | Average AgI | Grain size | Distribution | Aspect ratio | C/S ratio | AgI in C/S |
|---|---|---|---|---|---|---|
| A | 4.0% | 0.45 μm | 27% | 1 | 1/3 | 13/1 |
| B | 8.9% | 0.70 μm | 14% | 1 | 3/7 | 25/2 |
| C | 10.0% | 0.75 μm | 30% | 2 | 1/2 | 24/3 |
| D | 16.0% | 1.05 μm | 35% | 2 | 4/6 | 40/0 |
| E | 10.0% | 1.05 μm | 35% | 3 | 1/2 | 24/3 |
| F | 4.0% | 0.25 μm | 28% | 1 | 1/3 | 13/1 |
| G | 14.0% | 0.75 μm | 25% | 2 | 1/2 | 42/0 |
| H | 14.5% | 1.30 μm | 25% | 3 | 37/63 | 34/3 |
| I | 1.0% | 0.07 μm | 15% | 1 | Uniform grains | |

(Remark)
Average AgI: Average silver iodide content
Grain size: Average grain size
Distribution: Distribution coefficient of grain size
Aspect ratio: Ratio of grain size to grain thickness
C/S ratio: Ratio of silver content in core/shell
AgI in C/S: Silver iodide content in core/shell To each of the layers, the following W-1, W-2, W-3, P-4, P-5, F-1, F-2, F-3, F-4, F-6, F-7, F-8, F-9, F-10, F-11, F-12, F-13, an iron salt, a lead salt, a gold salt, a platinum salt, an iridium salt and a rhodium salt were added to improve stability, handling, pressure-resistance, antimycotic activity, antibacterial activity, antistatic or coating characteristics.

The additives are shown below.

EX-1

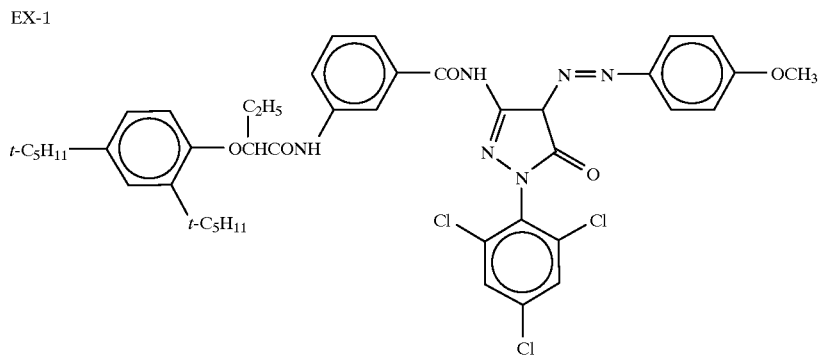

EX-2
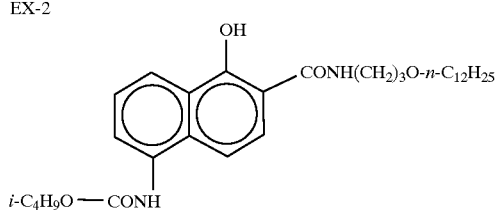
EX-3
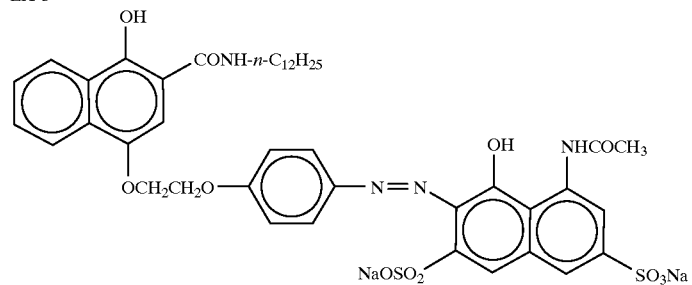
EX-4
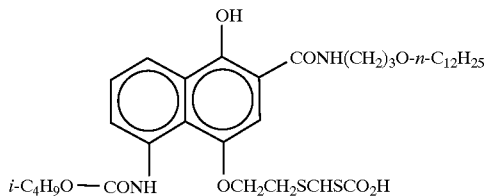
EX-5
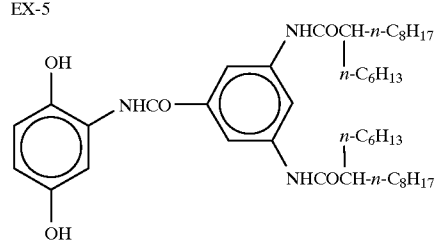
EX-6
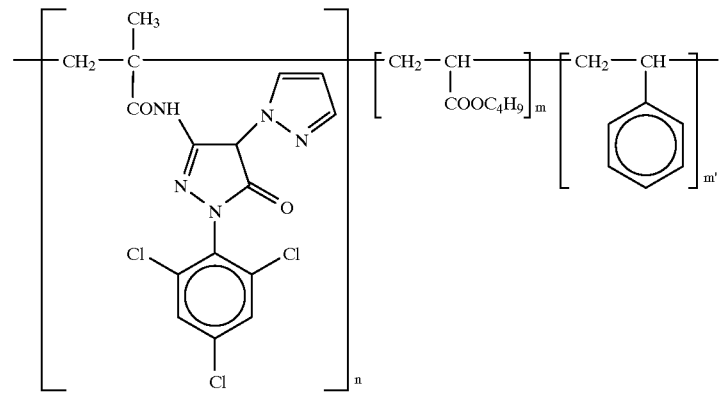
n = 50
m = 25
m' = 25
Molecular weight = about 20,000

-continued
EX-7
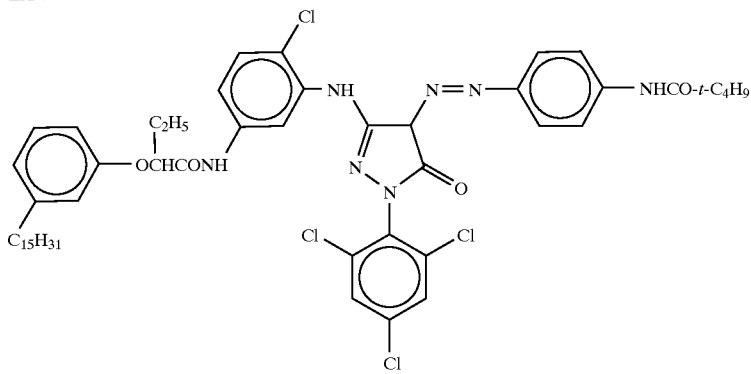
EX-8
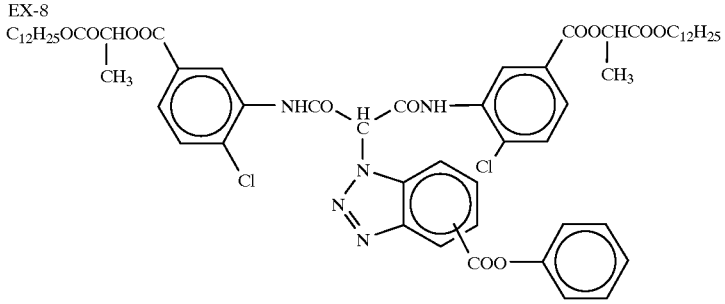
EX-9
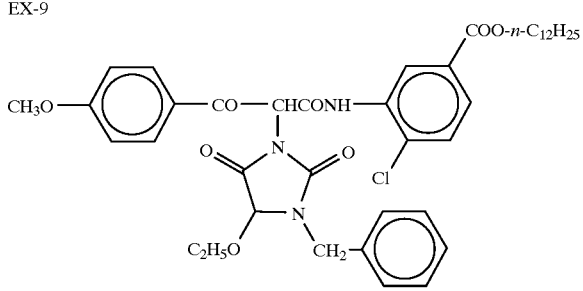
EX-10
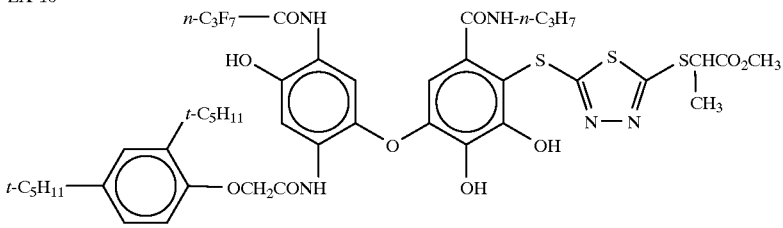
EX-11
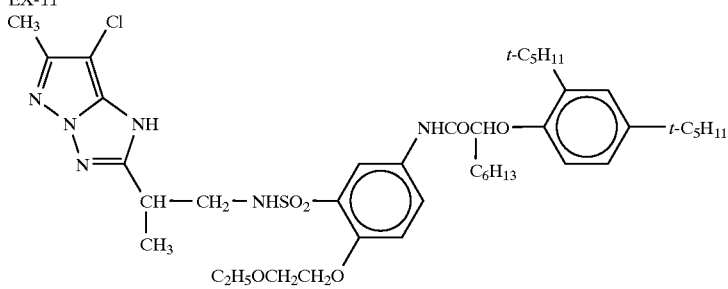

-continued
EX-12
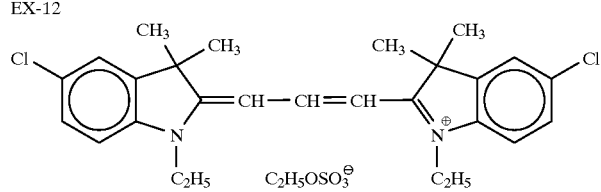
EX-13
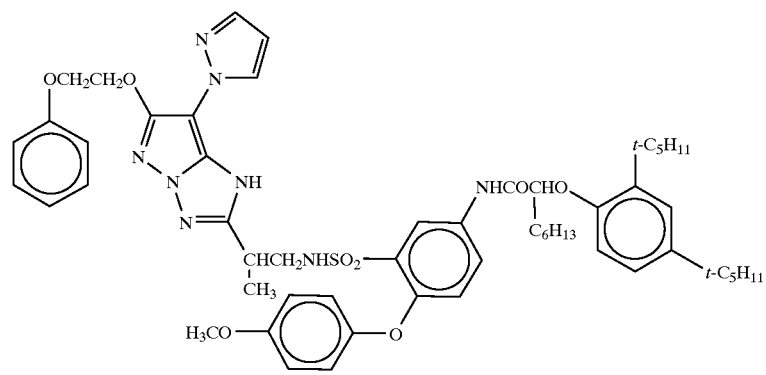
EX-14
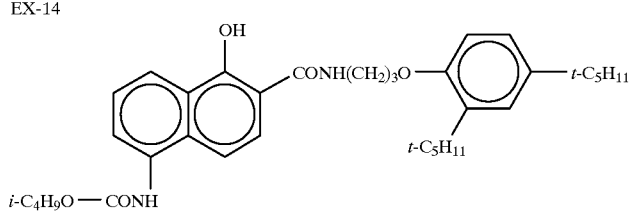
EX-15
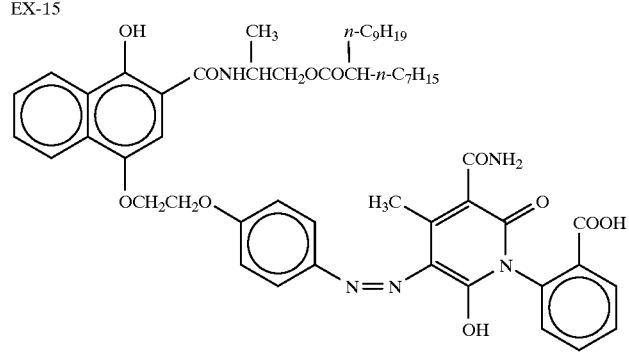
U-1
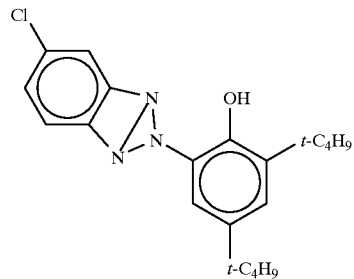

-continued
U-2
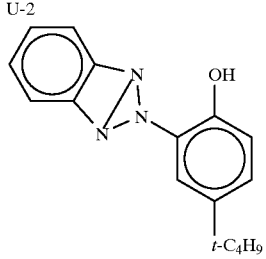
U-3
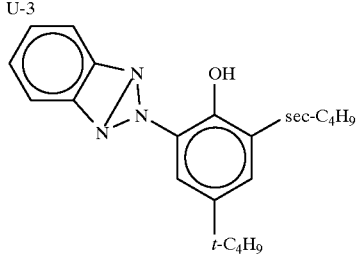
U-4
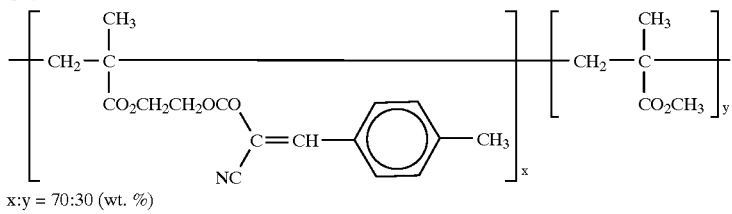
x:y = 70:30 (wt. %)
U-5
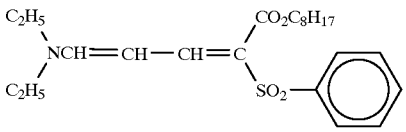
HBS
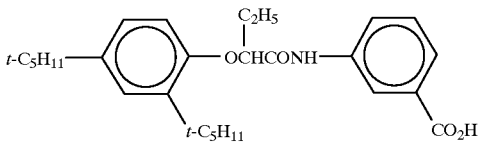
Sensitizing dye I
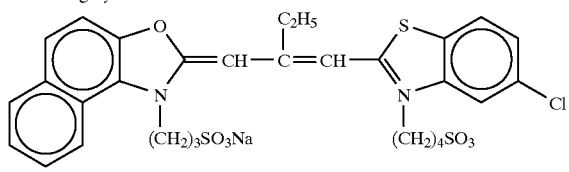
Sensitizing dye II
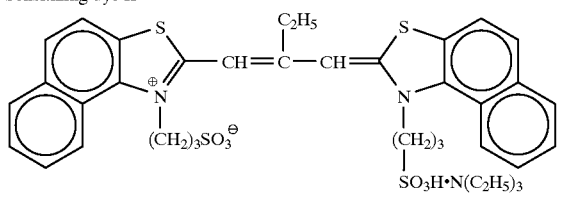

-continued
Sensitizing dye III
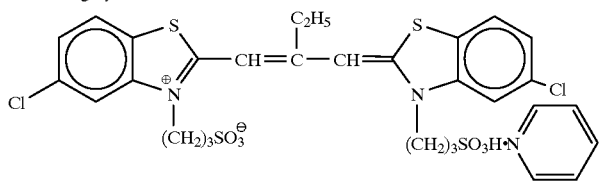
Sensitizing dye IV
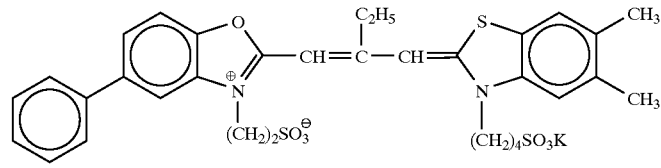
Sensitizing dye V
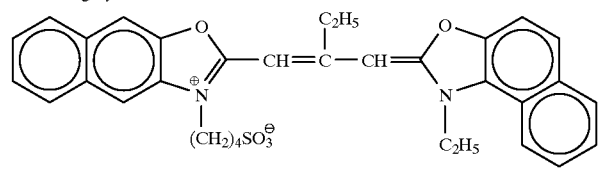
Sensitizing dye VI
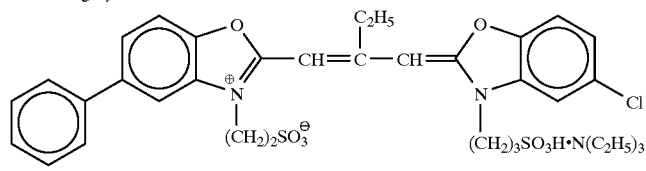
Sensitizing dye VII
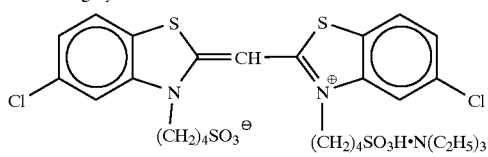
S-1
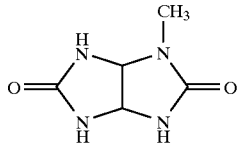
H-1
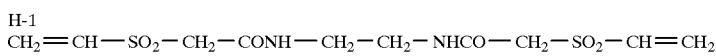
P-1
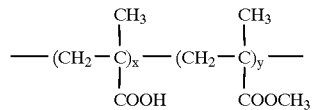
x/y = 10/90
P-2
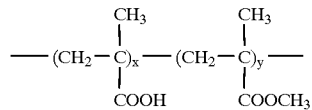
x/y = 40/60

-continued
P-3
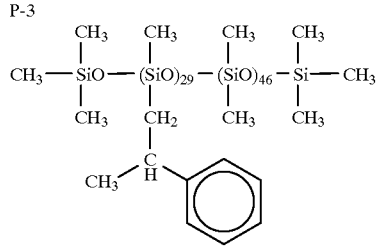
P-4
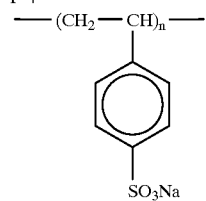
P-5
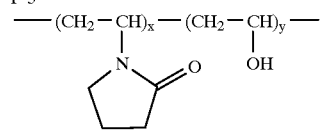
x/y = 70/30
W-1
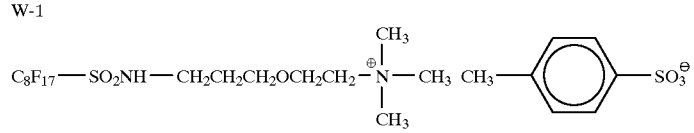
W-2
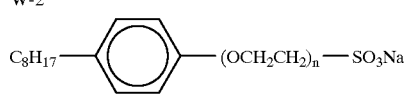
n = 2–4
W-2
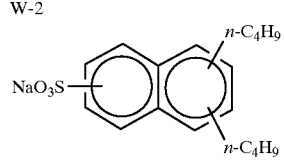
F-1
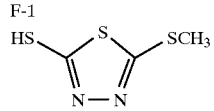
F-2
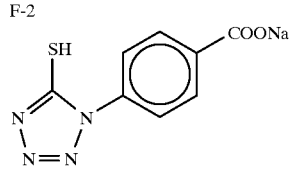
F-3
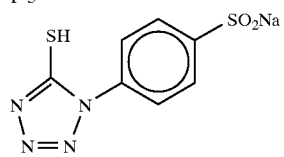

-continued
F-4
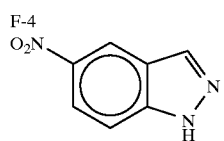
F-5
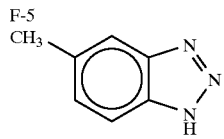
F-6
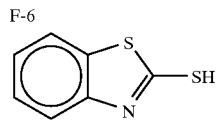
F-7
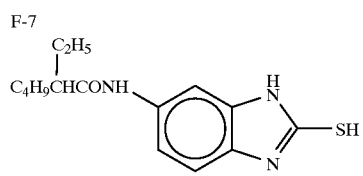
F-8
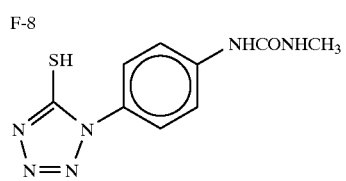
F-9
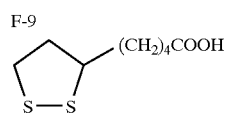
F-10
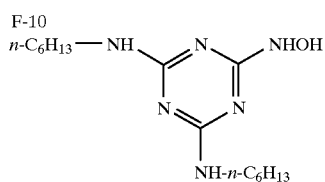
F-11
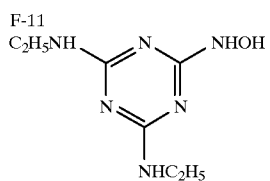
F-12
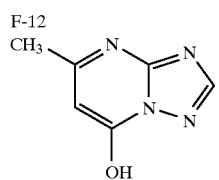
F-13
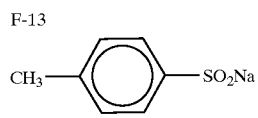

A sample No. 102 was prepared in the same manner as in the preparation of the sample No. 101, except that the following comparative compound A-x was coated in an amount of 0.20 g/m² in the tenth layer in place of the yellow colloidal silver.

Comparative Compound A-x

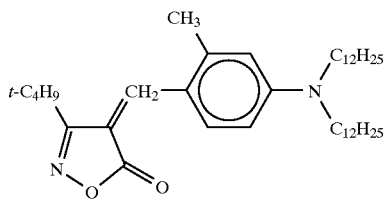

The comparative compound A-x was used in the form of an emulsion, which was prepared in the following manner.

The following components of the solution 1 were dissolved at 60° C. Separately, the following components of the solution 2 were dissolved at 50° C. The solution 2 was added to the solution 1, and the mixture was stirred at 12,000 rpm for 5 minutes by using a high speed stirring device (Homogenizer DX-11, Nippon Seiki K.K.), while keeping the temperature at 50° C. To the stirred mixture, 16 ml of water was added. The mixture was cooled to 40° C. Ethyl acetate was removed under reduced pressure to obtain an emulsion of the dye having the average particle size of 0.22 μm.

| Solution 1 | | |
|---|---|---|
| Dye (compound A) | 150 | mg |
| The following high boiling point organic solvent 1 | 150 | mg |
| Ethyl acetate | 4.5 | ml |
| Sodium dodecylbenzensulfonate | 90 | mg |
| Solution 2 | | |
| Gelatin (Ca content: 30 ppm) | 1.2 | g |
| Water | 8.7 | ml |
| 3.4 Wt. % methanol solution of the following compound 1 | 0.12 | ml |

High boiling point organic solvent 1

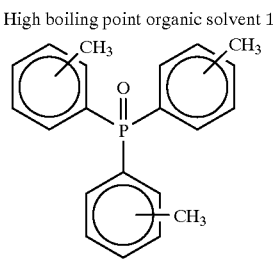

Compound 1

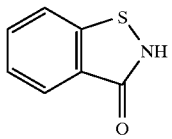

Sample Nos. 103 to 108 were prepared in the same manner as in the preparation of the sample No. 102, except that the compounds A-2, A-6, A-10, A-18, A-23 and A-26 were respectively used in place of the comparative compound A-x. The amounts of the compounds were the same mole of the comparative compound A-x.

The obtained samples were exposed to white light through an optical wedge. The exposed samples were developed according to the following method (A) by using an automatic developing machine. The machine was so adjusted that the total amount of the replenisher was three times the volume of the mother liquid tank.

| Method (A) | | | | |
|---|---|---|---|---|
| Process | Time | Temp. | Replenisher* | Tank |
| Development | 3'15" | 38° C. | 33 ml | 20 l |
| Bleaching | 6'30" | 38° C. | 25 ml | 40 l |
| Washing | 2'10" | 24° C. | 1,200 ml | 20 l |
| Fixing | 4'20" | 38° C. | 25 ml | 30 l |
| Washing (1) | 1'05" | 24° C. | (2) to (1)** | 10 l |
| Washing (2) | 1'00" | 24° C. | 1,200 ml | 10 l |
| Stabilizing | 1'05" | 38° C. | 25 ml | 10 l |
| Drying | 4'20" | 55° C. | | |

(Remark)
*: The amount of the replenisher per 1 m of a sample (width: 35 mm)
**: Counter current from (2) to (1)

The compositions of the solutions are shown below.

| | Mother liquid | | Replenisher | |
|---|---|---|---|---|
| Color developing solution | | | | |
| Diethylenetriaminetetraacetic acid | 1.0 | g | 1.1 | g |
| 1-Hydroxyethlidene-1,1-diphosphonic acid | 3.0 | g | 3.2 | g |
| Sodium sulfite | 4.0 | g | 4.4 | g |
| Potassium carbonate | 30.0 | g | 37.0 | g |
| Potassium bromide | 1.4 | g | 0.7 | g |
| Potassium iodide | 1.5 | mg | — | |
| Sulfate salt of hydroxylamine | 2.4 | g | 2.8 | g |
| Sulfate salt of 4-(N-ethyl-N-β-hydroxy-ethylamino)-2-methylaniline | 4.5 | g | 5.5 | g |
| Water (to make up to) | 1.0 l | | 1.0 l | |
| pH | 10.05 | | 10.10 | |
| Bleaching solution | | | | |
| Iron(III) sodium ethylenediamine-tetraacetate trihydrate | 100.0 | g | 120.0 | g |
| Disodium ethylenediaminetetraacetate | 10.0 | g | 10.0 | g |
| Ammonium bromide | 140.0 | g | 160.0 | g |
| Ammonium nitrate | 30.0 | g | 35.0 | g |
| Ammonium water (27%) | 6.5 | ml | 4.0 | ml |
| Water (to make up to) | 1.0 l | | 1.0 l | |
| pH | 6.0 | | 5.7 | |
| Fixing solution | | | | |
| Disodium ethylenediaminetetraacetate | 0.5 | g | 0.7 | g |
| Sodium sulfite | 7.0 | g | 8.0 | g |
| Sodium bisulfite | 5.0 | g | 5.5 | g |
| Aqueous solution (70%) of ammonium thiosulfate | 170.0 | ml | 200.0 | ml |
| Water (to make up to) | 1.0 l | | 1.0 l | |
| pH | 6.7 | | 6.6 | |
| Stabilizing solution | | | | |
| Formalin (37%) | 2.0 | ml | 3.0 | ml |
| Polyoxyethylene p-monononylphenyl ether | 0.3 | g | 0.45 | g |
| Disodium ethylenediaminetetraacetate | 0.05 | g | 0.08 | g |
| Sodium bisulfite | 5.0 | g | 5.5 | g |
| Water (to make up to) | 1.0 l | | 1.0 l | |
| pH | 5.0–8.0 | | 5.0–8.0 | |

After the samples were processed, the density of the fogged area of the blue sensitive layer ($D_B$ (min)) was measured to evaluate the decoloring characteristic of the dye, which was evaluated as a relative value to the sample No. 101 (±0).

Further, the sensitivity of the green sensitive layer was measured as the logarithm of the reciprocal number of the exposure required for forming the density of the fog+0.2. The logarithm was evaluated as a relative value to the sample No. 101 (±0).

The results are set forth in Table 1.

TABLE 1

| Sample | Dye | $D_B$ (min) | Sensitivity (G) |
|---|---|---|---|
| 101 | Yellow silver | ±0 | ±0 |
| 102 | A-x | ±0.18 | +0.07 |
| 103 | A-2 | +0.0 | +0.09 |
| 104 | A-6 | ±0.0 | +0.12 |
| 105 | A-10 | ±0.0 | +0.10 |
| 106 | A-18 | ±0.0 | +0.08 |
| 107 | A-23 | ±0.0 | +0.14 |
| 108 | A-26 | ±0.0 | +0.18 |

As is evident from the results shown in Table 1, the samples according to the present invention give the values of $D_B$ (min) in the same as the value of the sample 101. Accordingly, the dyes used in the present invention are excellent in the decoloring characteristic. Further, the sensitivity of the green sensitive layer is greatly improved in the samples according the present invention. The sensitivity is improved because a dye has an excellent absorption.

EXAMPLE 2

The samples prepared in Example 1 were evaluated in the same manner as in Example 1, except that the samples were processed as follows. As a result, the value of $D_B$ (min) of the sample No. 102 was further increased to cause a serious problem about the decoloring characteristic. On the other hand, the sample Nos. 103 to 108 according to the present invention have no problems about the values of $D_B$ (min). Further, the sensitivity of the green sensitive layer was increased in the samples of the invention in the same manner as in Example 1.

Method (B)

| Process | Time | Temp. | Replenisher* | Tank |
|---|---|---|---|---|
| Development | 3'15" | 37.8° C. | 25 ml | 10 l |
| Bleaching | 45" | 38° C. | 5 ml | 4 l |
| Bleach-fix (1) | 45" | 38° C. | (2) to (1)** | 4 l |
| Bleach-fix (2) | 45" | 38° C. | 30 ml | 4 l |
| Washing (1) | 20" | 38° C. | (2) to (1)** | 2 l |
| Washing (2) | 20" | 38° C. | 30 ml | 2 l |
| Stabilizing | 20" | 38° C. | 20 ml | 2 l |
| Drying | 1'00" | 55° C. | | |

(Remark)
*: The amount of the replenisher per 1 m of a sample (width: 35 mm)
**: Counter current from (2) to (1)

All the overflowed bleaching solution was introduced into the bleach-fixing bath (2).

The bleach-fixing solution was introduced into the washing process in an amount of 2 ml based 1 m length of the photographic material (width: 35 mm).

The compositions of the solutions are shown below.

| | Mother liquid | | Replenisher | |
|---|---|---|---|---|
| Color developing solution | | | | |
| Diethylenetriaminetetraacetic acid | 5.0 | g | 6.0 | g |
| Sodium sulfite | 4.0 | g | 5.0 | g |
| Potassium carbonate | 30.0 | g | 37.0 | g |
| Potassium bromide | 1.3 | g | 0.5 | g |
| Potassium iodide | 1.2 | mg | — | |
| Sulfate salt of hydroxylamine | 2.0 | g | 3.6 | g |
| Sulfate salt of 4-(N-ethyl-N-β-hydroxy-ethylamino)-2-methylaniline | 4.7 | g | 6.2 | g |
| Water (to make up to) | 1.0 | l | 1.0 | l |
| pH | 10.00 | | 10.15 | |
| Bleaching solution | | | | |
| Iron(III) ammonium 1,3-diaminopropane-tetraacetate monohydrate | 144.0 | g | 206.0 | g |
| 1,3-Diaminopropanetetraacetic acid | 2.8 | g | 4.0 | g |
| Ammonium bromide | 84.0 | g | 120.0 | g |
| Ammonium nitrate | 17.5 | g | 25.0 | g |
| Ammonium water (27%) | 10.0 | ml | 1.8 | ml |
| Acetic acid (98%) | 51.1 | ml | 73.0 | ml |
| Water (to make up to) | 1.0 | l | 1.0 | l |
| pH | 4.3 | | 3.4 | |
| Bleach-fixing solution | | | | |
| Iron(III) ammonium ethylenediamine-tetraacetate dihydrate | 50.0 | g | — | |
| Disodium ethylenediaminetetraacetate | 5.0 | g | 25.0 | g |
| Ammonium sulfite | 12.0 | g | 20.0 | g |
| Aqueous solution (700 g per l) of ammonium thiosulfate | 170.0 | ml | 200.0 | ml |
| Ammonium water (27%) | 6.0 | ml | 15.0 | ml |
| Water (to make up to) | 1.0 | l | 1.0 | l |
| pH | 6.8 | | 8.0 | |

Washing Water (Both Mother Liquid and Replenisher)

Running water was introduced into a mixed bed column charged with an H-type strong acidic cation exchanger resin (Amberlite IR-120B, Rohm & Haas) and an OH-type storing basic anion exchanger resin (Amberlite IRA-400, Rohm & Haas). Water was treated in the column to decrease calcium ion content and magnesium ion to not more than 3 mg per liter respectively. Sodium isocyanurate dichloride (20 mg per liter) and sodium sulfate (150 mg per liter) were added to the treated water. The pH of the obtained washing solution was in the range of 6.5 to 7.5.

| Stabilizing solution (both mother liquid and replenisher) | | |
|---|---|---|
| Formalin (37%) | 1.2 | ml |
| $C_{10}H_{21}$—O—$(CH_2CH_2O)_{10}$—H (surface active agent) | 0.4 | g |
| Ethylene glycol | 1.0 | g |
| Water (to make up to) | 1.0 | l |
| pH | 5.0–8.0 | |

EXAMPLE 3

Preparation of Emulsion A ({111})AgBr Tabular Grains)

To 1 liter of water, 6.0 g of potassium bromide and 7.0 g of low molecular weight gelatin (weight average molecular weight: 15,000) were added. The mixture was placed in a vessel. To the vessel, 37 ml of silver nitrate aqueous solution (silver nitrate: 4.00 g) and 38 ml of potassium bromide aqueous solution (potassium bromide: 5.9 g) were added for 37 seconds according to a double jet method while keeping the temperature at 55° C. Further, 18.6 g of gelatin was added to the mixture. The mixture was heated to 70° C., and 89 ml of silver nitrate aqueous solution (silver nitrate: 9.80 g) was added to the mixture. The mixture was subjected to physical ripening for 10 minutes while keeping the temperature. To the mixture, 6.5 ml of acetic acid (100%) was added.

To the resulting mixture, 435 ml of silver nitrate aqueous solution (silver nitrate: 153 g) and 677 ml of potassium bromide aqueous solution (potassium bromide: 573 g) were added for 35 minutes according to a controlled double jet method while keeping the pAg of 8.5 to complete the addition of the silver nitrate solution (the addition of the potassium bromide aqueous solution was stopped when the addition of the silver nitrate solution was completed). To the mixture, 15 ml of 2 N potassium thiocyanate solution was added. The mixture was subjected to physical ripening for 5 minutes while keeping the temperature. The mixture was cooled to 35° C.

Thus monodispersed silver bromide (AgBr) {111} tabular grains were formed. The ratio of the projected area of {100} tabular grains having an aspect ratio of 2 to 30 to the projected area of the total silver halide grains was 95%. The average aspect ratio of the {100} tabular grains having an aspect ratio of 2 to 30 was 12.0. The average grain size based on the projected area of the {100} tabular grains having an aspect ratio of 2 to 30 was 1.20 $\mu$m. The average thickness of the {100} tabular grains having an aspect ratio of 2 to 30 was 0.10 $\mu$m. The distribution coefficient of the grain size based on the projected area of the {100} tabular grains having an aspect ratio of 2 to 30 was 15.5%.

Chemical Sensitization

The prepared grains were subjected to chemical sensitization while stirring the grains at 56° C. First, sodium ethanethiosulfonate ($1\times10^{-4}$ mol per 1 mol of silver halide) was added to the grains. Next, silver bromide fine grains having the average grain size of 0.10 $\mu$m (1.0 mol % based on the total silver amount) were added to the grains. After 5 minutes, 1 wt. % potassium iodide aqueous solution ($1\times10^{-3}$ mol per 1 mol of silver halide) was added to the grains. After 3 minutes, thiourea dioxide ($1\times10^{-46}$ mol per 1 mol of silver halide) was added to the grains. The mixture was left for 22 minutes to conduct reduction sensitization. To the grains, 4-hydroxy-6-methyl-1,3,3a,7-tetrazaindene ($3\times10^{-4}$ mol per mol Ag), the following sensitizing dye 1 ($1\times10^{-3}$ mol per mol Ag), the following sensitizing dye 2 ($1\times10^{-5}$ mol per mol Ag) and the following sensitizing dye 3 ($3\times10^{-4}$ Mol per mol Ag) were added. Next, calcium chloride ($1\times10^{-2}$ mol per mol Ag) was added to the grains. Further, chloroauric acid ($1\times10^{-5}$ mol per mol Ag) and potassium thiocyanate ($3.0\times10^{-3}$ mol per mol Ag) were added to the grains. Furthermore, sodium thiosulfate ($6\times10^{-6}$ mol per mol Ag) and the following selenium compound 1 ($4\times10^{-6}$ mol per mol Ag) were added to the grains. After 3 minutes, nucleic acid (0.5 g per mol Ag) was added to the grains. After 40 minutes, the following water-soluble mercapto compound 1 was added to the grains. The mixture was cooled to 35° C. Thus the chemical sensitization was completed.

Sensitizing dye 1

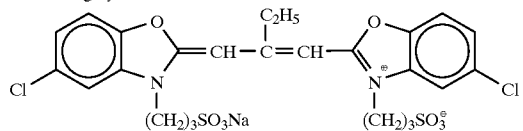

Sensitizing dye 2

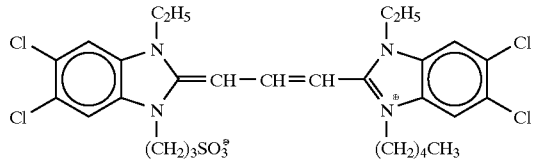

Sensitizing dye 3

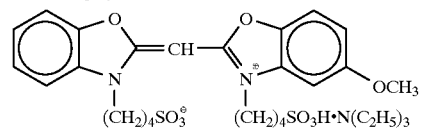

Selenium compound 1

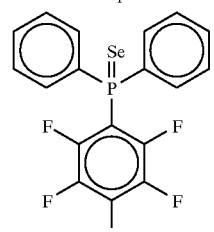

Water-soluble mercapto compound 1

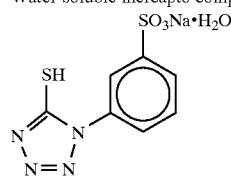

Preparation of Coating Solution for Emulsion Layer

To the above-prepared emulsion, the following compounds were added to prepare a coating solution for an emulsion layer. The following core/shell latex has the core/shell weight of 50/50, the core made of styrene/butadiene copolymer (copolymerization weight ratio: 37/63), the shell made of styrene/2-acetoacetoxyethyl methacrylate copolymer (copolymerization weight ratio: 84/16) and the average grain size of about 0.1 $\mu$m.

| Additives of coating solution | Amount (per 1 mol of AgX) | |
| --- | --- | --- |
| Gelatin (including gelatin contained in the emulsion) | 50.0 | g |
| Dextran (average molecular weight: 39,000) | 10.0 | g |
| Sodium polyacrylate (average molecular weight: 400,000) | 5.1 | g |
| Sodium polystyrenesulfonate (average molecular weight: 600,000) | 1.2 | g |
| Potassium iodide | 78 | mg |

-continued

| Additives of coating solution | Amount (per 1 mol of AgX) |
|---|---|
| 1,2-Bis(vinylsulfonylacetamido)ethane (hardening agent) | Amount adjusted to the swelling ratio of 90% |
| The following additive 1 | 42.1 mg |
| The following additive 2 | 10.3 g |
| The following additive 3 | 0.11 g |
| The following additive 4 | 8.5 mg |
| The following additive 5 | 0.43 g |
| The following additive 6 | 0.04 g |
| Core/shell latex | 70 g |
| The following dye emulsion a (solid content of dye) | 0.50 g |
| The following dye emulsion m (solid content of dye) | 30 mg |
| pH (adjusted with sodium hydroxide) | 6.1 |

Additive 1

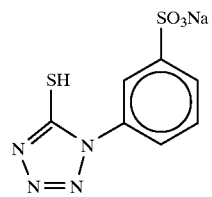

Additive 2

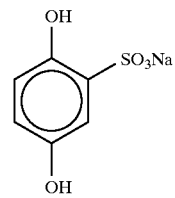

Additive 3

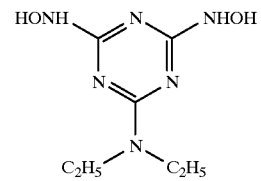

Additive 4

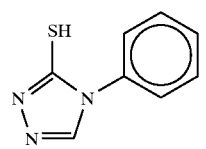

Additive 5

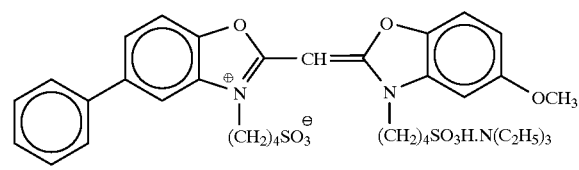

Additive 6

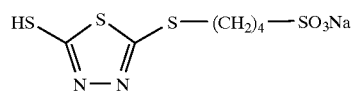

Preparation of Dye Emulsion a

With 333 g of ethyl acetate, 60 g of the following dye 1, 62.8 g of 2,4-diamylphenol, 62.8 g of dicyclohexylphthalate were mixed. The mixture was stirred at 60° C. to prepare a solution. To the solution, 65 ml of 5 wt. % aqueous solution of sodium dodecylbenzenesulfonate, 94 g of gelatin and 581 ml of water were added. The mixture was stirred at 60° C. for 30 minutes to prepare an emulsion. To the emulsion, 2 g of methyl p-hydroxybenzoate and 6 liter of water were added. The mixture was cooled to 40° C. The mixture was condensed to the total amount of 2 kg by using an ultrafiltration laboratory module (ACP 1050, Asahi Chemical Industry Co., Ltd.). To the resulting emulsion, 1 g of methyl p-hydroxybenzoate was added to obtain a dye emulsion a.

Dye 1

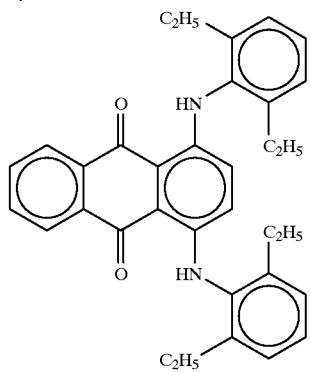

Preparation of Dye Emulsion m

To a solvent comprising 10 ml of tricresyl phosphate and 20 ml of ethyl acetate, 10 g of the following dye 2 was dissolved. The solution was emulsified in 15 wt. % aqueous gelatin solution containing 750 mg of the following anionic surface active agent 1 to prepare a dye dispersion m.

Dye 2

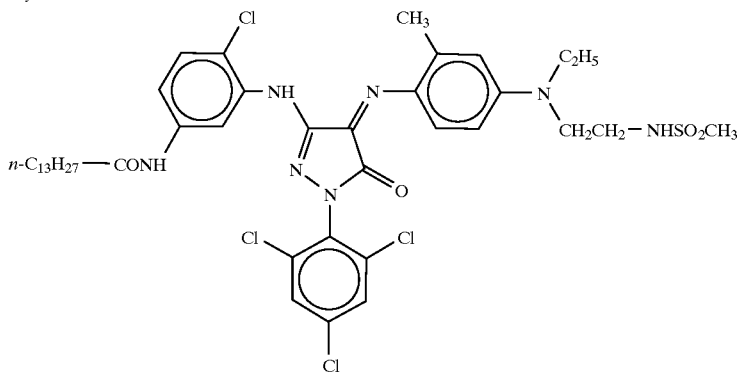

Anionic surface active agent 1

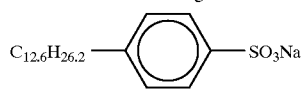

Preparation of Coating Solution for Dye Layer

A coating solution was prepared by using the following components.

| Coating solution for dye layer | Coating amount |
|---|---|
| Gelatin | 0.25 g/m$^2$ |
| The following additive 8 | 1.4 mg/m$^2$ |
| Sodium polystyrenesulfonate (average molecular weight: 600,000) | 5.9 mg/m$^2$ |
| The following dye dispersion i (solid content of dye) | 20 mg/m$^2$ |

Additive 8

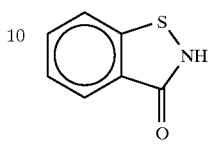

Preparation of Dye Dispersion i

The following dye 3 was treated as a wet cake without drying. To the dye 3 (dry solid weight: 6.3 g), 25 wt. % aqueous solution of the following dispersing aid V (dry solid weight: 30 wt. % of the dry solid weight of the dye) was added. Water was added to the mixture to the total amount of 63.3 g. The mixture was well stirred to form a slurry. The slurry and 100 ml of zirconia beads (average size: 0.5 mm) were placed in a vessel. The slurry was stirred for 6 hours in a dispersing machine (1/16G sand grinder mill, Aimex Co., Ltd.). To the slurry, water was added to adjust the dye concentration of 8 wt. % to obtain a dye dispersion.

Photogrpahic gelatin was added to the dye dispersion to adjust the solid dye content of 5 wt. % and the gelatin content of 5 wt. %. To the dispersion, the additive 8 (2,000 ppm to gelatin) was added as an antiseptic. The mixture was cooled to form gel, and stored at the cooled temperature.

The obtained dye dispersion i contained solid particles of the insoluble dye, which has a maximum absorption at 915 nm. The average particle size of the dye dispersion i was 0.4 μm.

Dye 3

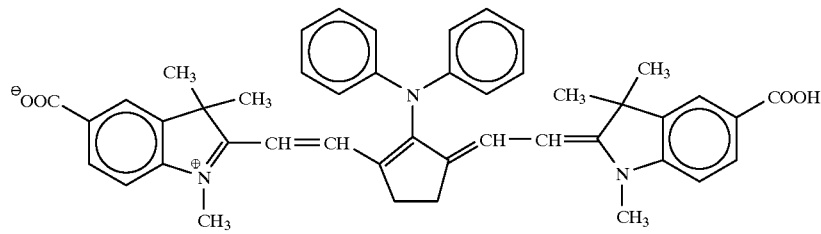

Dispersing aid V

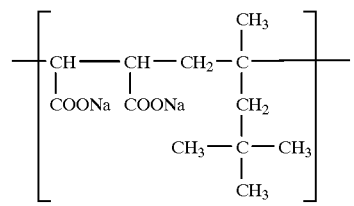

Preparation of Coating Solution for Surface Protective Layer

A coating solution was prepared by using the following components.

| Coating solution for surface layer | Coating amount (g/m$^2$) |
|---|---|
| Gelatin | 0.780 |
| Sodium polyacrylate (average molecular weight: 400,000) | 0.025 |
| Sodium polystyrenesulfonate (average molecular weight: 600,000) | 0.0012 |
| The following matting agent 1 (average particle size: 3.7 μm) | 0.072 |
| The following matting agent 2 (average particle size: 0.7 μm) | 0.010 |
| The following additive 9 | 0.018 |
| The following additive 10 | 0.037 |
| The following additive 11 | 0.0068 |
| The following additive 12 | 0.0032 |
| The following additive 13 | 0.0012 |
| The following additive 14 | 0.0022 |
| The following additive 15 | 0.030 |
| Surface active agent (proquicel, ICI) | 0.0010 |
| pH (adjusted with sodium hydroxide) | 6.8 |

Matting agent 1 (x/y/z = 76.3/17.5/6.2)
Matting agent 2 (x/y/z = 70/15/15)

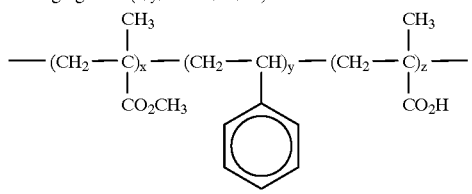

Additive 9

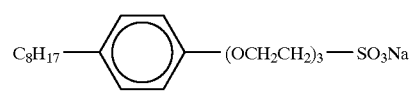

Additive 10

| Coating solution for surface layer | Coating amount (g/m$^2$) |
|---|---|

Additive 11

$C_{17}H_{35}CONCH_2CH_2CHSO_3Na$
$\quad\quad\quad\;\;|$
$\quad\quad\quad\;\;CH_3$ Additive 12

$F-(CF_2)_8-SO_2N-(CH_2CH_2O)_{15}-H$
$\quad\quad\quad\quad\quad\;\;|$
$\quad\quad\quad\quad\quad\;\;C_3H_7$ Additive 13

$F-(CF_2)_8-SO_2N-(CH_2CH_2O)_4-(CH_2)_4-SO_3Na$
$\quad\quad\quad\quad\quad\;\;|$
$\quad\quad\quad\quad\quad\;\;C_3H_7$ Additive 14

[structure: mercapto-tetrazole with phenyl-COONa substituent]

Additive 15

[structure: 2-chloro-1,4-benzoquinone]

Preparation of Support and Undercoating Layer

A biaxially stretched polyethylene terephthalate film (containing the dye 1 in the amount of 0.04 wt. %) having the thickness of 175 μm was subjected to corona discharge treatment. The following coating solution for the undercoating layer was coated on the film (coating amount: 4.9 ml per m$^2$) using a wire bar coater. The coating solution was dried at 185° C. for 1 minute.

Next, an undercoating layer was formed on the reverse side of the support in the same manner.

| Coating solution for undercoating layer | |
| --- | --- |
| Butadiene/styrene copolymer latex (solid content: 40 wt. %, copolymerization ratio: 31/69) containing the following additive 16 (0.4 wt. % of the solid content) as an emulsifying and dispersing agent | 158 ml |
| 4 Wt. % aqueous solution of sodium salt of 2,4-dichloro-6-hydroxy-s-triazine | 41 ml |
| Distilled water | 801 ml |

Additive 16

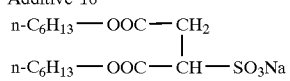

Preparation of Dye Dispersion B

The following dye 4 was treated in a ball mill (according to the description of Japanese Patent Provisional Publication No. 61(1988)-197943).

Dye 4

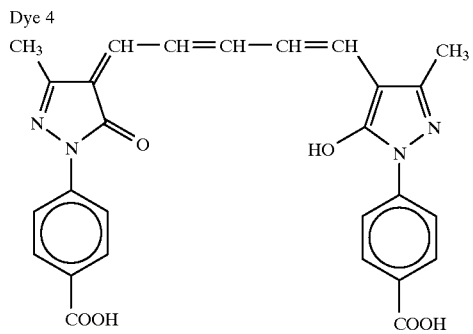

In a ball mill of 2 liter, 434 of water and 6.7 wt. % aqueous solution of a surface active agent (Triton X-200) was placed. To the solution, 20 g of the dye 4 was added. To the mixture, 400 ml of zirconium oxide ($ZrO_2$) beads (diameter: 2 mm) were added. The mixture was crushed for 4 days. To the mixture, 160 g of 12.5 wt. % aqueous gelatin solution was added. After the mixture was defoamed, $ZrO_2$ beads were filtered out. The obtained dye dispersion was observed. As a result, the crushed dye has the broad particle size range of 0.05 to 1.15 μm. The average particle size was 0.37 μm. The dispersion was centrifuged to remove the dye particles of 0.9 μm or larger. Thus the dye dispersion B was obtained.

Formation of Crossover Cutting Layer A

On each of the undercoating layers of the support, the following coating solution for the crossover cutting layer A was coated by using a wire bar coater, and dried at 155° C.

| Coating solution for crossover cutting layer A | |
| --- | --- |
| Gelatin | 80 mg/m² |
| Dye dispersion B | (set forth in Table 2) |
| The following additive 17 | 1.8 mg/m² |
| The additive 8 | 0.27 mg/m² |
| Matting agent (polymethyl methactylate particles, average particle size: 2.5 μm) | 2.5 mg/m² |

Additive 17

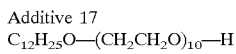

Preparation of Sample No. 301

The coating solutions for the dye layer, the emulsion layer and the surface protective layer were coated on both side of the support having the undercoating layer and the crossover cutting layer A according to a simultaneous extrusion method, and dried. The coated silver amount on one side was adjusted to 1.4 g per m². Thus a silver halide photographic material (sample No. 301) was prepared.

Preparation of Coating Solution for Crossover Cutting Layer B

The dyes B-2, B-6, B-23 and B-26 according to the present invention was emulsified in the same manner as in Example 1 to obtain dye emulsions.

The coating solutions for crossover cutting layers B were prepared by using the following components.

| Coating solution for crossover cutting layer B | |
| --- | --- |
| Gelatin | 0.24 mg/m² |
| Dye dispersion | (set forth in Table 2) |
| Sodium polystyrenesulfonate (average molecular weight: 600,000) | 19 mg/m² |
| 1,2-Bis(vinylsulfonylacetamido) ethane (hardening agent) | 7.6 mg/m² |

Preparation of Sample Nos. 302 to 305

The coating solutions for the cross over cutting layer B, the dye layer, the emulsion layer and the surface protective layer were coated on both side of the support having the undercoating layer according to a simultaneous extrusion method, and dried. The coated silver amount on one side was adjusted to 1.4 g per m². Thus silver halide photographic materials (sample Nos. 302 to 305) were prepared.

Preparation of Developing Solution

The following developing solution (developing agent: sodium erythrobate) was prepared.

| Composition of developing solution | | |
| --- | --- | --- |
| Diethylenetriaminetetraacetic acid | 8.0 | g |
| Sodium sulfite | 20.0 | g |
| Sodium carbonate monohydrate | 52.0 | g |
| Potassium carbonate | 55.0 | g |
| Sodium erythrobate | 60.0 | g |
| 4-Hydroxymethyl-4-methyl-1-phenyl-3-pyrazolidone | 13.2 | g |
| 3,3'-Diphenyl-3,3'-dithiopropionic acid | 1.44 | g |
| Diethylene glycol | 50.0 | g |
| The following additive 18 | 0.15 | g |
| The following additive 19 | 0.30 | g |
| Water (to make up to) | 2 | liter |
| pH (adjusted with sodium hydroxide) | 10.1 | |

Additive 18

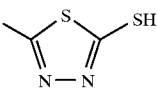

Additive 19

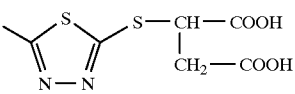

Preparation of Developing Replenisher

The above-prepared developing solution was used as the developing replenisher.

Preparation of Developing Mother Liquid

To 2 liters of the developing solution, the following starter solution was added (55 ml per 1 liter of the developing solution) to prepare a developing mother liquid (pH: 9.5)

| Starter solution | | |
| --- | --- | --- |
| Potassium bromide | 11.1 | g |
| Acetic acid | 10.8 | g |
| Water (to make up to) | 100 | ml |

Preparation of Condensed Fixing Solution

The following condensed fixing solution was prepared.

| Composition of condensed fixing solution | | |
| --- | --- | --- |
| Water | 0.5 | l |
| Ethylenediaminetetraacetic acid dihydrate | 0.05 | g |
| Sodium thiosulfate tetrahydrate | 200 | g |
| Sodium bisulfite | 98.0 | g |
| Sodium hydroxide | 2.9 | g |
| pH (adjusted with sodium hydroxide) | 5.4 | |
| Water (to make up to) | 1 | liter |

Preparation of Fixing Replenisher

The condensed fixing solution was diluted twice with a waste fluid from the first washing process to used the diluted solution as the fixing replenisher.

Preparation of Fixing Mother Liquid

With water, 2 liters of the condensed fixing solution was diluted to obtain 4 liters of the fixing mother liquid (pH: 5.4).

Preparation of Washing Replenisher

With distilled water, 0.3 g of glutaraldehyde and 0.5 g of diethylenetriaminetetraacetic acid were diluted. The solution was adjusted to pH 4.5 with sodium hydroxide to obtain the washing replenisher.

Process of Photographic Material

An automatic developing machine (CEPROS-S, Fuji Photo Film Co., Ltd.) was reconstructed to adjust the washing tank according to a two-stages countercurrent method. The washing replenisher was supplied to the second washing tank. The opening rate of the developing tank and the fixing tank was adjusted to 0.02. The volume of the washing tanks was 6 liter. The drying process was conducted according to a heat roller method.

The samples were treated in the automatic developing machine using the above-prepared developing mother liquid, the fixing mother liquid and the washing replenisher. Each of the developing replenisher, the fixing replenisher and the washing replenisher was supplied to the machine in an amount 65 ml based on 1 m² of the photographic material. The processing conditions are shown below.

| Process | Temperature | Time |
| --- | --- | --- |
| Development | 35° C. | 8 seconds |
| Fixing | 35° C. | 7 seconds |
| First washing | 30° C. | 5 seconds |
| Second washing | 25° C. | 5 seconds |
| Drying | 85° C. (surface of rollers) | 3 seconds |
| Total | | 38 seconds |

Evaluation of Photographic Characteristic

Each of the photographic materials was exposed to light from both sides for 0.1 second by using an X-ray ortho screen (HG-M, Fuji Medical System Co., Ltd.). The photographic materials were developed and dried. The sensitivities of the photogrpahic materials were evaluated.

The relative sensitivity was measured based on the density of the fog (including the base density) +1.0 after the samples were processed. The sensitivity was evaluated as a relative value to the sample No. 301 (100). The results are set forth in Table 2.

Evaluation of Remaining Color

After the samples were processed, the absorption spectrum was measured. The remaining color was evaluated as the absorption at 550 nm. The results are set forth in Table 2.

TABLE 2

| Sample No. | Dye | Amount of dye | Sensitivity | Remaining color |
| --- | --- | --- | --- | --- |
| 301 | Dye 4 | 10 mg/m² | 100 | 0.123 |
| 302 | B-2 | 6.6 mg/m² | 113 | 0.023 |
| 303 | B-6 | 10 mg/m² | 102 | 0.059 |
| 304 | B-23 | 9.7 mg/m² | 108 | 0.031 |
| 305 | B-26 | 9.5 mg/m² | 115 | 0.013 |

As is evident from the results shown in Table 2, a silver halide photographic material of high sensitivity and low remaining color can be prepared by using a compound of the present invention as a dye.

EXAMPLE 4

Preparation of Silver Halide Emulsion

First, the following first to third solutions were prepared.

| First solution | | |
| --- | --- | --- |
| Water | 1 | liter |
| Gelatin | 20 | g |
| Sodium chloride | 3.0 | g |
| 1,3-Dimethylimidazolidine-2-thion | 20 | mg |
| Sodium benzenethiosulfonate | 8 | mg |
| Second solution | | |
| Water | 400 | ml |
| Silver nitrate | 100 | g |
| Third solution | | |
| Water | 400 | ml |
| Sodium chloride | 27.1 | g |
| Potassium bromide | 21.0 | g |
| 0.001 Wt. % aqueous solution of ammonium hexachloroiridate (III) | 20 | ml |
| 0.001 Wt. % aqueous solution of potassium hexachloroiridate (III) | 6 | ml |

To the first solution, the second and third solutions were simultaneously added for 15 minutes while stirring and keeping 42° C. and pH of 4.5. To the formed nuclear grains, the following fourth and fifth solutions were added for 15 minutes. Further, 0.15 g of potassium iodide was added to form grains.

| Fourth solution | | |
|---|---|---|
| Water | 400 | ml |
| Silver nitrate | 100 | g |
| Fifth solution | | |
| Water | 400 | ml |
| Sodium chloride | 27.1 | g |
| Potassium bromide | 21.0 | g |
| 0.1 Wt. % aqueous solution of potassium hexacyanoferrate (II) | 10 | ml |

The grains were washed with water according to a conventional flocculation method. To the emulsion, 40 g of gelatin was added.

After the emulsion was adjusted to pH 5.7 and pAg 7.5, 1.0 mg of sodium thiosulfate, 4.0 mg of chloroauric acid, 1.5 mg of triphenylphosphineselenide, 8 mg of sodium benzenethiosulfonate and 2 mg of sodium benzenethiosulfinate were added. The emulsion was subjected to chemical sensitization at 55° C. to obtain the optimum sensitivity.

Further, 4-hydroxy-6-methyl-1,3,3a,7-tetrazaindene (stabilizer) and phenoxyethanol (antiseptic) were added to the emulsion to obtain silver chloroiodobromide cubic emulsion. The silver chloride content was 70 mol % and the average grain size was 0.25 μm.

Preparation of Coating Sample (Sample No. 401)

The following sensitizing dye 11 ($3.8 \times 10^{-4}$ mol per mol Ag) was added to the silver halide emulsion to conduct spectral sensitization.

Sensitizing dye 11

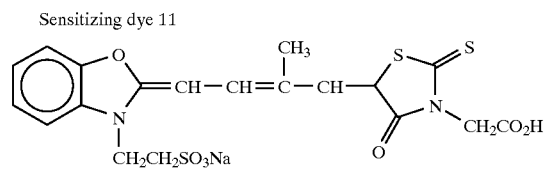

Further, potassium bromide ($3.4 \times 10^{-4}$ mol per mol Ag), the following compound 11 ($3.2 \times 10^{-4}$ mol per mol Ag), the following compound 12 ($8.0 \times 10^{-4}$ mol per mol Ag), hydroquinone ($1.2 \times 10^{-2}$ mol per mol Ag), citric acid ($3.0 \times 10^{-3}$ mol per mol Ag), the following compound 13 ($1.0 \times 10^{-4}$ mol per mol Ag), the following compound 14 ($6.0 \times 10^{-4}$ mol per mol Ag), a polyethyl acrylate latex (35 wt. % of gelatin), colloidal silica of average particle size of 10 mμ (20 wt. % of gelatin) and the following compound 15 (4 wt. % of gelatin) were added to the emulsion to prepare a coating solution for the emulsion layer.

Compound 11

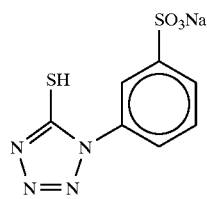

Compound 12

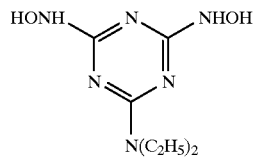

Compound 13

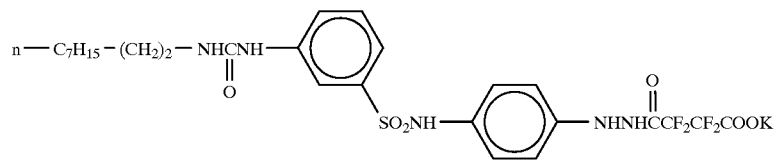

Compound 14

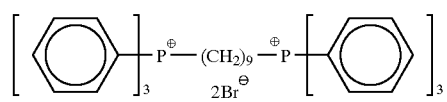

Compound 15

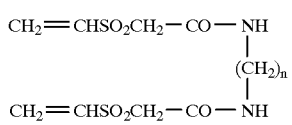

Mixture of n = 2 and n = 3 (3:1)

The coating solution for the emulsion layer was coated on the undercoating layer of a polyester support having the undercoating layer, the backing layer and the electroconductive layer (described below). The coated silver amount was 3.7 g per m$^2$, and the gelatin coating amount was 1.6 g per m$^2$.

The following upper protective layer and the following lower protective layer were formed on the emulsion layer.

| Composition of upper protective layer | | |
|---|---|---|
| Gelatin | 0.3 | g/m$^2$ |
| Silica matting agent (average particle size: 3.5 μm) | 25 | mg/m$^2$ |
| Gelatin dispersion of the following compound 16 | 20 | mg/m$^2$ |
| Colloidal silica (particle size: 10 to 20 μm) | 30 | mg/m$^2$ |
| The following compound 17 | 5 | mg/m$^2$ |
| Sodium dodecylbenzenesulfonate | 20 | mg/m$^2$ |
| The following compound 18 | 20 | mg/m$^2$ |
| Composition of lower protective layer | | |
| Gelatin | 0.5 | g/m$^2$ |
| The following compound 19 | 15 | mg/m$^2$ |
| 1,5-dihydroxy-2-benzaldoxime | 10 | mg/m$^2$ |
| Polyethyl acrylate latex | 150 | mg/m$^2$ |

Compound 16

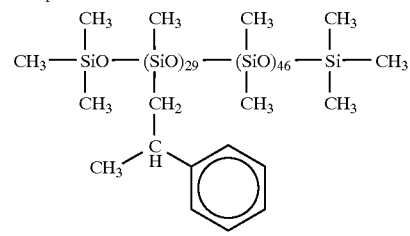

Compound 17

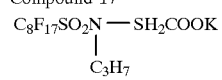

Compound 18

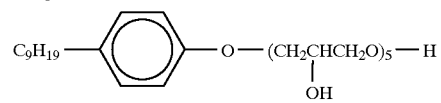

Compound 19

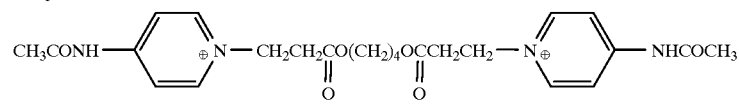

The composition of the undercoating layer (provided between the support and the emulsion layer) is shown below.

| Composition of undercoating layer | | |
|---|---|---|
| Gelatin | 0.5 | g/m² |
| Polyethyl acrylate latex | 150 | mg/m² |
| The compound 15 | 40 | mg/m² |
| The following compound CY-1 | 10 | mg/m² |

Compound CY-1

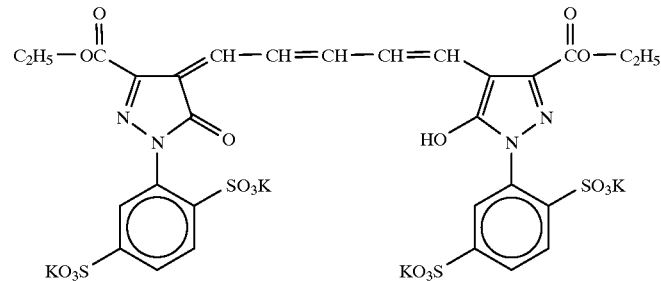

The compositions of the backing layer and the electroconductive layer (provided on the back side of the support) are shown below.

| Composition of backing layer | | |
|---|---|---|
| Gelatin | 3.3 | g/m² |
| Sodium dodecylbenzenesulfonate | 80 | mg/m² |
| The following compound Y | 40 | mg/m² |
| The following comparative dye M | 20 | mg/m² |
| The following compound CY-2 | 90 | mg/m² |
| 1,3-Divinylsulfonyl-2-propanol | 60 | mg/m² |
| Polymethyl methacrylate fine particles (average particle size: 6.5 μm) | 30 | mg/m² |
| The compound 15 | 120 | mg/m² |
| Composition of electroconductive layer | | |
| Gelatin | 0.1 | g/m² |
| Sodium dodecylbenzenesulfonate | 20 | mg/m² |
| SnO₂/Sb (weight ratio: 9/1, average particle size: 0.25 μm) | 200 | mg/m² |

Compound Y

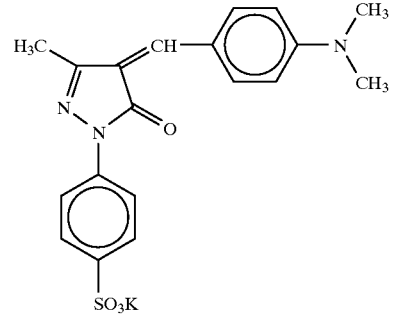

Comparative dye M

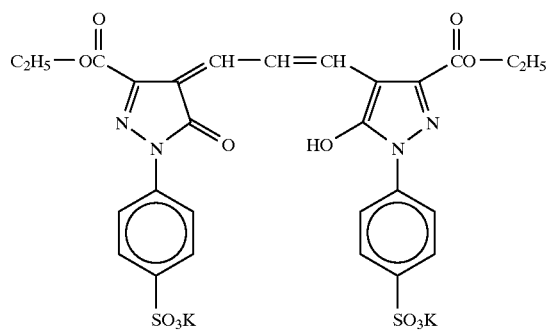

Compound CY-2

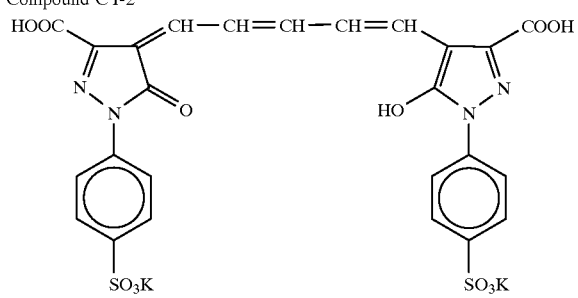

Thus the sample No. 401 was prepared.

Next, the compounds B-2, B-6, B-10, B-18, B-23 and B-26 according to the present invention was emulsified in the same manner as in Example 1. The sample Nos. 402 to 407 were prepared in the same manner as in the preparation of the sample No. 401, except that the obtained dye emulsions were used in place of the comparative dye M added to the backing layer.

Evaluation of Photographic Characteristic

The sample Nos. 401 to 407 were exposed to light through an interference filter (peak: 550 nm) and a step wedge by using a xenon flash lump for $10^{-6}$ second. The samples were developed, fixed, washed and dried in an automatic developing machine (FG-710NH, Fuji Photo Film Co., Ltd.) under the following conditions.

| Process | Characteristic test Temp. | Time | Remaining color test Temp. | Time |
|---|---|---|---|---|
| Development | 35° C. | 14 seconds | 35° C. | 9 seconds |
| Fixing | 35° C. | 9.7 seconds | 35° C. | 6.2 seconds |
| Washing | 25° C. | 9 seconds | 10° C. | 5.8 seconds |
| Squeezing | | 2.4 seconds | | 1.5 second |
| Drying | 55° C. | 8.3 seconds | 55° C. | 5.3 seconds |
| Total | | 43.4 seconds | | 27.8 seconds |

The compositions of the developing solution and the fixing solution are shown below.

| Composition of developing solution | | |
|---|---|---|
| Diethylenetriaminetetraacetic acid | 2 | g |
| Potassium carbonate | 33 | g |
| Sodium carbonate | 28 | g |
| Sodium hydrogen carbonate | 25 | g |
| Sodium erythrobate | 45 | g |
| N-methyl-p-aminophenol | 7.5 | g |
| 5-Methylbenztriazole | 0.004 | g |
| 1-Phenyl-5-mercaptotetrazole | 0.02 | g |
| Sodium sulfite | 2 | g |
| Water (to make up to) | 1 | liter |
| pH | 9.7 | |
| Composition of condensed fixing solution | | |
| Ammonium thiosulfate | 360 | g |
| Disodium ethylenediaminetetracetate dihydrate | 0.09 | g |
| Sodium thiosulfate tetrahydrate | 33.0 | g |
| Sodium metasulfite | 57.0 | g |
| Sodium hydroxide | 37.2 | g |
| Acetic acid (100%) | 90.0 | g |
| Tartaric acid | 8.7 | g |
| Sodium gluconate | 5.1 | g |
| Aluminum sulfate | 25.2 | g |
| Water (to make up to) | 1 | liter |
| pH | 4.85 | |

With 2 parts of water, 1 part of the condensed fixing solution was diluted to prepare a fixing solution (pH: 4.8).

The sensitivity and the remaining color of the samples were evaluated in the same manner as in Example 3. The results are set forth in Table 3.

TABLE 3

| Sample No. | Dye | Relative sensitivity | Remaining color |
|---|---|---|---|
| 401 | Comparative dye M | 100 | 0.078 |
| 402 | B-2 | 105 | 0.021 |

TABLE 3-continued

| Sample No. | Dye | Relative sensitivity | Remaining color |
|---|---|---|---|
| 403 | B-6 | 112 | 0.008 |
| 404 | B-10 | 110 | 0.010 |
| 405 | B-18 | 104 | 0.025 |
| 406 | B-23 | 115 | 0.004 |
| 407 | B-26 | 120 | 0.002 |

As is evident from the results shown in table 3, a silver halide photographic material of high sensitivity and low remaining color can be prepared by using a compound of the present invention as a dye.

We claim:

1. An arylidene compound represented by the formula (I):

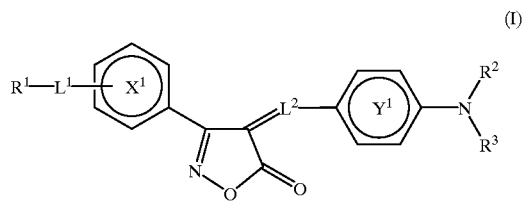

(I)

in which $L^1$ is a divalent linking group consisting of at least one —NH— and at least one of —CO— and —SO$_2$—; $L^2$ is monomethine, trimethine or pentamethine, each of which may be substituted with an alkyl group, an alkoxy group, amino, an alkylamino group, an amido group or an aryl group; $R^1$ is an alkyl group, an aryl group or a heterocyclic group, each of which may be substituted with a halogen atom, cyano, hydroxyl, an alkyl group, an alkoxycarbonyl group, an aryl group, a heterocyclic group, amino, an alkylamino group, an acyl group, an amido group, a sulfonamido group, a carbamoyl group or a sulfamoyl group; each of $R^2$ and $R^3$ independently is hydrogen, an alkyl group or an aryl group, the number of the total carbon atoms contained in $R^2$ and $R^3$ is not more than 20, and the alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group; the benzene ring $X^1$ may be further substituted with a halogen atom, cyano, hydroxyl, an alkyl group substituted with a halogen atom, an alkoxy group, an acyl group, a sulfonamido group or a sulfamoyl group; and the benzene ring $Y^1$ may be further substituted with an alkyl group, an alkoxy group, an aryl group, amino, an alkylamino group or an amido group.

2. The arylidene compound as claimed in claim 1, wherein $L^1$ is a divalent linking group selected from the group consisting of —NHCO—, —CONH—, —NHSO$_2$—, —SO$_2$NH—, —SO$_2$NHCO— and —CONHSO$_2$—.

3. The arylidene compound as claimed in claim 1, wherein $L^2$ is monomethine, trimethine or pentamethine, each of which has no substituent groups.

4. The arylidene compound as claimed in claim 1, wherein each of $R^2$ and $R^3$ independently is an alkyl group, the number of the total carbon atoms contained in $R^2$ and $R^3$ is not more than 20, and the alkyl group may be substituted with a halogen atom, cyano, hydroxyl, carboxyl, an alkoxy group, an alkylamino group, a sulfonamido group or a sulfamoyl group.

5. An arylidene compound represented by the formula (II):

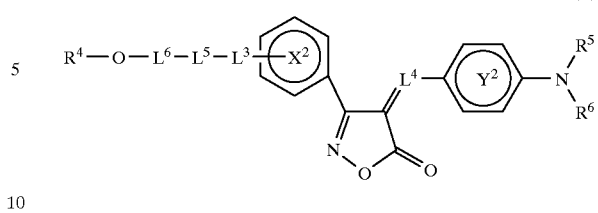

(II)

in which $L^3$ is a divalent linking group consisting of at least one —NH— and at least one of —CO— and —SO$_2$—; $L^4$ is monomethine, trimethine or pentamethine, each of which may be substituted with an alkyl group, an alkoxy group, amino, an alkylamino group, an amido group or an aryl group; $L^5$ is an alkylene group or an arylene group, each of which may be substituted with a halogen atom or hydroxyl; $L^6$ is a divalent linking group selected from the group consisting of —NH—, —O—, —CO—, —SO$_2$—, an alkylene group, an arylene group and a combination thereof, and the alkylene group and the arylene group may be substituted with a halogen atom or hydroxyl; $R^4$ is hydrogen or an alkyl group; each of $R^5$ and $R^6$ independently is hydrogen, an alkyl group or an aryl group, the number of the total carbon atoms contained in $R^5$ and $R^6$ is not more than 20, and the alkyl group and the aryl group may be substituted with a halogen atom, cyano, hydroxyl, carboxyl, an alkyl group, an alkoxy group, an alkoxycarbonyl group, an alkylamino group, a sulfonamido group or a sulfamoyl group; the benzene ring $X^2$ may be further substituted with a halogen atom, cyano, hydroxyl, an alkyl group substituted with a halogen atom, an alkoxy group, an acyl group, a sulfonamido group or a sulfamoyl group; and the benzene ring $Y^2$ may be further substituted with an alkyl group, an alkoxy group, an aryl group, amino, an alkylamino group or an amido group.

6. The arylidene compound as claimed in claim 5, wherein $L^3$ is a divalent linking group selected from the group consisting of —NHCO—, —CONH—, —NHSO$_2$—, —SO$_2$NH—, —SO$_2$NHCO— and —CONHSO$_2$—.

7. The arylidene compound as claimed in claim 5, wherein $L^4$ is monomethine, trimethine or pentamethine, each of which has no substituent groups.

8. The arylidene compound as claimed in claim 5, wherein $L^5$ is an arylene group, which may be substituted with a halogen atom or hydroxyl.

9. The arylidene compound as claimed in claim 5, wherein $L^6$ is a divalent linking group selected from the group consisting of $L^{61}$, $L^{62}$ and $L^{63}$:

$L^{61}$: —(an alkylene group)—O—(an alkylene group)—O—CO—

$L^{62}$: —(an alkylene group)—O—CO—

$L^{63}$: —(an alkylene group) —NH—CO— in which the alkylene group may be substituted with a halogen atom or hydroxyl.

10. The arylidene compound as claimed in claim 5, wherein $R^4$ is hydrogen.

11. The arylidene compound as claimed in claim 5, wherein each of $R^5$ and $R^6$ independently is an alkyl group, the number of the total carbon atoms contained in $R^5$ and $R^6$ is not more than 20, and the alkyl group may be substituted with a halogen atom, cyano, hydroxyl, carboxyl, an alkoxy group, an alkylamino group, a sulfonamido group or a sulfamoyl group.

12. An arylidene compound represented by the formula (Ia):

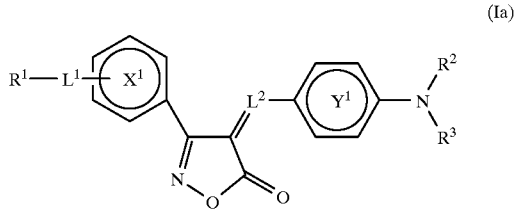

in which $L^1$ is a divalent linking group consisting of at least one —NH— and at least one of —CO— and —SO$_2$—; $L^2$ is monomethine, trimethine or pentamethine, each of which may be substituted with an alkyl group, an alkoxy group, amino, an alkylamino group, an amido group or an aryl group; $R^1$ is an aryl group substituted with a halogen atom, cyano, hydroxyl, an alkyl group, an alkoxycarbonyl group, a hetero-cyclic group, amino, an alkylamino group, an acyl group, an amido group, a sulfonamido group, a carbamoyl group or a sulfamoyl group; each of $R^2$ and $R^3$ independently is hydrogen, an alkyl group or an aryl group, the number of the total carbon atoms contained in $R^2$ and $R^3$ is not more than 20, and the alkyl group and the aryl group may be substituted with a halogen atom, cyano, hydroxyl, carboxyl, an alkyl group, an alkoxy group, an alkylamino group, a sulfonamido group or a sulfamoyl group; the benzene ring $X^1$ may be further substituted with a halogen atom, cyano, hydroxyl, an alkyl group substituted with a halogen atom, an alkoxy group, an alkoxycarbonyl group, an acyl group, a sulfonamido group or a sulfamoyl group; and the benzene ring $Y^1$ may be further substituted with an alkyl group, an alkoxy group, an aryl group, amino, an alkylamino group or an amido group.

13. The arylidene compound as claimed in claim 12, wherein $L^2$ is a divalent linking group selected from the group consisting of —NHCO—, —CONH—, —NHSO$_2$, —SO$_2$NH—, —SO$_2$NHCO— and —CONHSO$_2$—.

14. The arylidene compound as claimed in claim 12, wherein $L^2$ is monomethine, trimethine or pentamethine, each of which has no substituent groups.

15. The arylidene compound as claimed in claim 12, wherein each of $R^2$ and $R^3$ independently is an alkyl group, the number of the total carbon atoms contained in $R^2$ and $R^3$ is not more than 20, and the alkyl group may be substituted with a halogen atom, cyano, hydroxyl, carboxyl, an alkoxy group, an alkylamino group, a sulfonamido group or a sulfamoyl group.

* * * * *